(12) United States Patent
Törnblom

(10) Patent No.: US 12,064,587 B2
(45) Date of Patent: Aug. 20, 2024

(54) CLOSED-SYSTEM TYPE FEMALE CONNECTOR, A METHOD FOR MANUFACTURE, AND A STOPCOCK HAVING SUCH FEMALE CONNECTORS

(71) Applicant: CYTO365 AB, Hoganas (SE)

(72) Inventor: Micael Törnblom, Viken (SE)

(73) Assignee: CYTO365 AB, Hoganas (SE)

( * ) Notice: Subject to any disclaimer, the term of this patent is extended or adjusted under 35 U.S.C. 154(b) by 0 days.

(21) Appl. No.: 18/011,822

(22) PCT Filed: Jun. 23, 2021

(86) PCT No.: PCT/EP2021/067223
§ 371 (c)(1),
(2) Date: Dec. 20, 2022

(87) PCT Pub. No.: WO2021/260050
PCT Pub. Date: Dec. 30, 2021

(65) Prior Publication Data
US 2023/0226340 A1   Jul. 20, 2023

(30) Foreign Application Priority Data

Jun. 24, 2020 (SE) .................... 2050751-3

(51) Int. Cl.
*A61M 39/26* (2006.01)
*A61M 39/22* (2006.01)

(52) U.S. Cl.
CPC ....... *A61M 39/26* (2013.01); *A61M 2039/229* (2013.01); *A61M 2039/267* (2013.01); *A61M 2207/00* (2013.01)

(58) Field of Classification Search
CPC ................ A61M 39/223; A61M 39/26; A61M 2039/224; A61M 2039/229;
(Continued)

(56) References Cited

U.S. PATENT DOCUMENTS 5,273,533 A * 12/1993 Bonaldo ............... A61M 39/04
604/905
5,330,435 A *  7/1994 Vaillancourt ......... A61M 39/26
241/149
(Continued)

FOREIGN PATENT DOCUMENTS

EP         0856331 A2    5/1998
WO    2005004974 A1    1/2005

OTHER PUBLICATIONS

IPER Chapter II report and WO2021260050—ISR.

*Primary Examiner* — Kevin F Murphy
*Assistant Examiner* — Jonathan J Waddy
(74) *Attorney, Agent, or Firm* — Fulwider Patton LLP

(57) ABSTRACT

A medical female connector (10) for controlling a fluid flow is disclosed, as well as a method for its manufacturing, and medical devices including such a female connector. A tubular plunger (40) and a flexible valve member (60) are inserted into a housing (20). A distal end (42) of the plunger (40) is located at a distance proximally from the distal end (22) of the housing (20). In a flow stop configuration, the flexible valve member (60) seals a flow path (44) through the tubular plunger (40). In a flow configuration, the valve member (60) is compressed by a male connector (90) and deformed by the plunger (40) to allow a fluid flow through the plunger (40). A frusto-conical female sealing surface (24) is arranged to form a seal with the male connector (90). An entrance opening (25) of the housing (20) presents a diameter equal to or larger than the maximum diameter (d1) of the female sealing surface (24).

14 Claims, 17 Drawing Sheets

SECTION A-A

(58) Field of Classification Search
CPC ...... A61M 2039/267; A61M 2039/268; A61M 2207/00; F16L 29/02; F16L 29/04; F16L 37/34; F16L 37/413
USPC .......................................................... 251/149
See application file for complete search history.

(56) References Cited

U.S. PATENT DOCUMENTS

| | | | | |
|---|---|---|---|---|
| 5,470,319 A | * | 11/1995 | Mayer | A61M 39/26 251/149.1 |
| 5,700,248 A | * | 12/1997 | Lopez | A61M 39/045 604/249 |
| 5,806,551 A | | 9/1998 | Meloul et al. | |
| 5,807,347 A | * | 9/1998 | Bonaldo | A61M 39/26 604/86 |
| 5,839,715 A | * | 11/1998 | Leinsing | A61M 39/045 604/905 |
| 6,158,458 A | * | 12/2000 | Ryan | F16L 41/03 137/903 |
| 7,056,308 B2 | * | 6/2006 | Utterberg | A61M 39/26 604/86 |
| 2004/0172006 A1 | * | 9/2004 | Bonaldo | A61M 39/26 604/523 |
| 2004/0186458 A1 | * | 9/2004 | Hiejima | A61M 39/26 604/411 |
| 2007/0066965 A1 | * | 3/2007 | Coambs | A61M 39/26 604/533 |
| 2008/0103484 A1 | * | 5/2008 | Hishikawa | A61M 39/26 604/533 |
| 2009/0182309 A1 | * | 7/2009 | Muffly | A61M 39/165 604/535 |
| 2014/0058336 A1 | * | 2/2014 | Burkholz | A61M 39/26 604/256 |
| 2014/0209197 A1 | * | 7/2014 | Carrez | F16L 29/005 137/798 |
| 2014/0228775 A1 | | 8/2014 | Burkholz et al. | |
| 2014/0246616 A1 | * | 9/2014 | Fangrow | F16L 29/00 251/148 |
| 2015/0265827 A1 | | 9/2015 | Keyser et al. | |

* cited by examiner

SECTION A-A

SECTION A-A

SECTION A-A

SECTION A-A

SECTION A-A

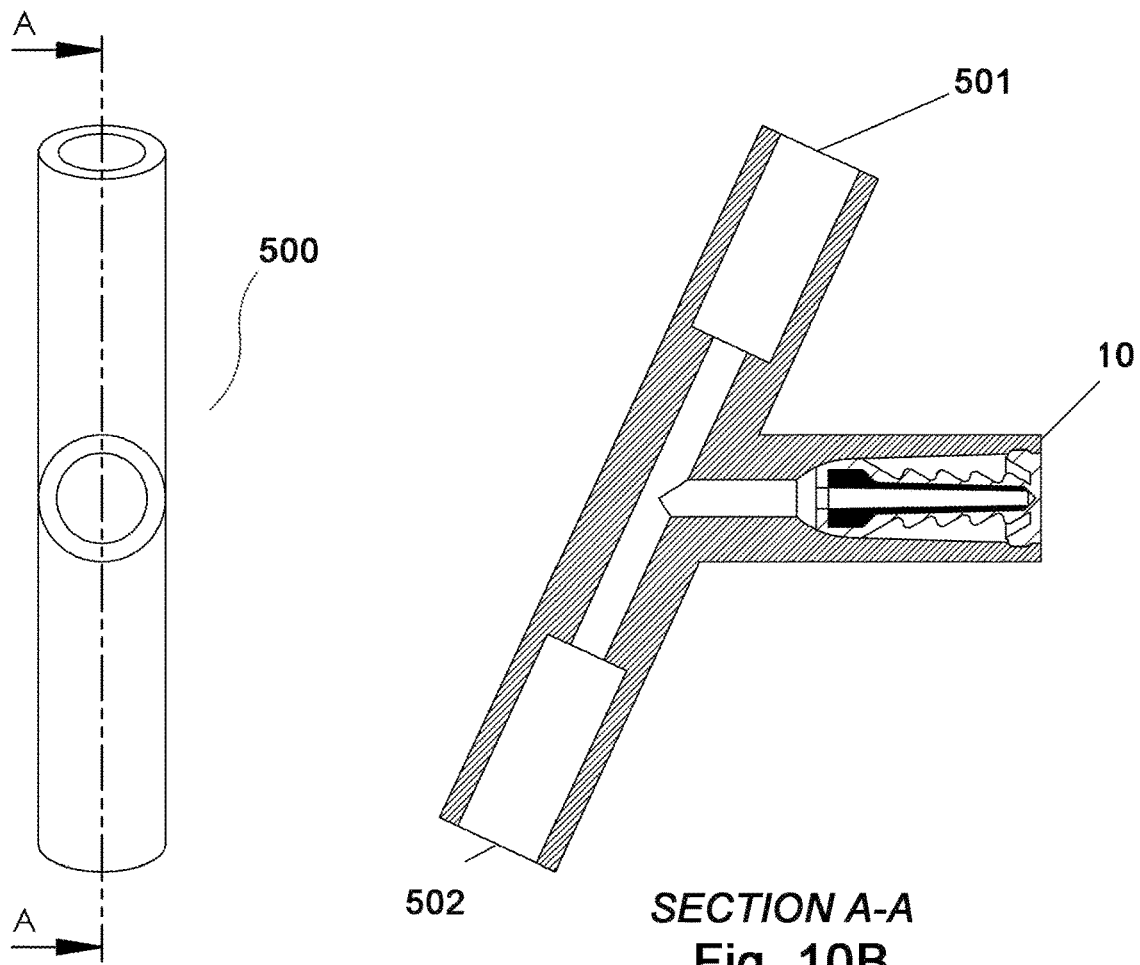
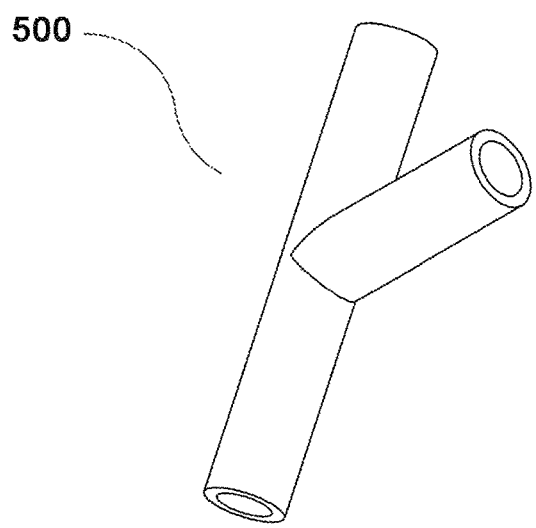
Fig. 10A
Fig. 10B  SECTION A-A
Fig. 10C

SECTION A-A

SECTION A-A

SECTION A-A

SECTION A-A

SECTION A-A

SECTION A-A

SECTION A-A

SECTION C-C

SECTION B-B

SECTION D-D

SECTION A-A

SECTION C-C

SECTION B-B

SECTION D-D

SECTION A-A

SECTION C-C

SECTION B-B

SECTION D-D

CLOSED-SYSTEM TYPE FEMALE CONNECTOR, A METHOD FOR MANUFACTURE, AND A STOPCOCK HAVING SUCH FEMALE CONNECTORS

CROSS-REFERENCES TO RELATED APPLICATIONS

This application is based on claims that benefit of priority to PCT/EP2021/067223, filed Jun. 23, 2021, which claims priority from Swedish Application No. 2050751-3, filed Jun. 24, 2020, incorporated by reference in their entirety.

TECHNICAL FIELD

The present disclosure generally relates to the field of small-bore connectors intended to be used for medical connections in intravascular applications or hypodermic connections in hypodermic applications of medical devices and accessories. Examples of use include luer slip connectors and luer lock connectors. More specifically, the inventive concept relates to a closed-system type female connector comprising an initially closed valve openable by connecting the female connector to a male connector. The inventive concept also relates to a method of manufacturing such a female connector, a male-female assembly including such a female connector, and a medical stopcock valve comprising one or more such female connectors.

BACKGROUND & SUMMARY OF INVENTION

There are many medical devices that require to be connected to an infusion line. Often, this is accomplished by luer access ports. Typically, a female luer connector receives a male luer connector. The female luer may be located on an infusion line where the infusion line is to be connected to a catheter giving access to the vascular system. A female luer connector may also be attached directly to a catheter giving access to the vascular system without any infusion line in between. The present inventive concept is not limited to where the medical female connector is placed.

At the inlet or entrance opening of a prior-art female connector there is typically either a cap, or a closed-system type valve member that occludes the inlet when the male connector is not connected. The inventive concept relates to medical female connectors of the closed-system type.

A closed-system type female connector is typically provided with an elastomeric valve member that initially occludes the female inlet port, and opens to allow a fluid passage when a male connector is introduced and coupled to the female inlet. A closed-system type valve member is normally structured and designed to close the fluid passage again if the male luer is disconnected, i.e. a valve with a return function. The female connector according to the inventive concept may be designed to present such a reclosing function. However, in some applications there may be a need for a closed system valve for opening only, especially for oncology where there is often a recommendation to not detach a connector once connected, even if there is a closed-system type valve.

For an elastomeric valve member designed to both open and close again, it is common to use a pre-slit opening in a proximal part of the elastomeric valve member. The inventive concept may be implemented accordingly. When the elastomeric membrane is seen in an unassembled (not in the housing) neutral relaxed state, the proximal end may be open or closed. When mounted in place, the proximal end is closed in its flow stop state. If the proximal end was an open end before it was mounted, it is now closed due to a fitting that require the elastomeric element to be compressed or deformed by the housing during assembly. The elastomeric membrane is opened when the it is compressed or deformed by a male Luer.

In a valve member designed to only open from an initially closed configuration, and not required to close again, the valve member doesn't need a pre-slit opening but could be instead be simply penetrated by a plunger upon connecting the male connector. The inventive concept may also be implemented accordingly. A combination of the above may also be possible, i.e. a design with no pre-slit, but still re-closable.

US 2016/0235961 A1 (Maffei) discloses a needle-free female connector. A tubular connector housing arranged to be coupled to an infusion line presents an entry and an internal pipe molded in one piece with the housing. A sealing element is movable between an occlusion position and an opening position. The entrance opening has a smaller cross-section dimension than the inner section of the housing, and the inner section of the housing is constant along its entire length, e.g. cylindrical. A female connector of this prior-art type presents both sealing problems and manufacturing problems as will be apparent from the following description.

In the light of the above, it is an object of the present inventive concept to address one or more of the above-mentioned disadvantages of the prior art.

According to a first aspect, there is provided a medical female connector for controlling a fluid flow, comprising:
a housing having an inner cavity defined by an inner surface of the housing and extending from an open proximal end of the housing to an open distal end of the housing, wherein:
  at least a part of the inner surface forms a frusto-conical female sealing surface, which defines a frusto-conical part of the inner cavity and which is arranged to form a seal with a male connector insertable in said frusto-conical part of the inner cavity, said frusto-conical female sealing surface having a maximum diameter at a proximal end of the female sealing surface and a minimum diameter at a distal end of the female sealing surface,
  the proximal end of the housing presents an entrance opening to the inner cavity with a diameter equal to or larger than the maximum diameter of the female sealing surface, and
  the minimum diameter of the female sealing surface is larger or equal to any diameter of the inner cavity between the distal end of the female sealing surface and the distal end of the housing;
a tubular plunger formed as a separate member from the housing and extending inside the inner cavity towards the entrance opening of the housing from a distal end of the plunger to a proximal end of the plunger, wherein said distal end of the plunger is located at a distance proximally from the distal end of the housing, and wherein the proximal end of the plunger is located inside said frusto-conical part of the inner cavity defined by the frusto-conical female sealing surface; and
a flexible valve member located in the inner cavity and movable between a flow stop configuration at which the valve member seals a flow path through the tubular plunger, and a flow configuration at which the flexible valve member is deformed by the plunger to allow a fluid flow through the plunger, wherein the flexible valve member at a distal end thereof presents a sealing part which forms a seal between the housing and the plunger and maintains the plunger positioned in relation to the housing.

According to a second aspect of the inventive concept, there is provided a method for manufacturing a medical female connector for controlling a fluid flow, said method comprising:

providing a housing having an inner cavity, which is defined by an inner surface of the housing and which extends from an open proximal end of the housing to an open distal end of the housing, wherein at least a part of the inner surface forms a frusto-conical female sealing surface, which defines a frusto-conical part of the inner cavity and which is arranged to form a seal with a male connector insertable in said frusto-conical part of the inner cavity, said frusto-conical female sealing surface and having a maximum diameter at a proximal end of the housing; and wherein the proximal end of the housing presents an entrance opening to the inner cavity with a diameter equal to or larger than the maximum diameter of the frusto-conical female sealing surface;

inserting a tubular plunger into the housing to a position in which the plunger extends inside the inner cavity, in a proximal direction towards the proximal end of the housing, from a distal end of the plunger to a proximal end of the plunger, wherein the distal end of the plunger is located at a distance proximally from the distal end of the housing and the proximal end of the plunger is located inside said frusto-conical part of the inner cavity defined by the frusto-conical female sealing surface; and inserting a flexible valve member into the inner cavity to a position where the flexible valve member is movable between a flow stop configuration at which the valve member seals a flow path through the tubular plunger, and a flow configuration at which the flexible valve member is deformed by the plunger to allow a fluid flow through the plunger, wherein, in the final manufactured female connector the flexible valve member at a distal end thereof presents a sealing part which forms a seal between the housing and the plunger and maintains the plunger positioned in relation to the housing.

In the present disclosure, the terms "proximal", "distal", "proximal direction", "distal direction", and the like should be interpreted as follows: The housing of the female connector has a proximal end where its entrance opening is located and where a male connector is to be received and connected to the female connector. The opposite end of the housing is the distal end of the housing. The distal end of the housing may be a free end, or it may be integrally formed with, or in some other way attached to, other equipment or parts, such as being integrally formed with the exterior of a medical stopcock valve housing. The proximal direction is the direction from the distal end towards the proximal entrance opening, and the distal direction is the opposite direction towards the distal end of the housing. Accordingly, the male connector is inserted into the female housing in the distal direction. Also, during the manufacture process, the plunger as well as the flexible valve member are inserted in the distal direction into the inner cavity. In embodiments where the inner cavity and the frusto-conical female sealing surface are circular symmetric, the term "axial" refers to the axis of symmetry extending from the proximal end to the distal end. In the description of stopcocks, "axial" refers to the axis of rotation of the rotary stopcock valve member.

A medical female connector according to the inventive concept may typically be implemented as a closed-system type connector, sometimes also referred to as needle-free connector, or LAD (Luer Activated Device), or LAV (Luer Activated Valve). The housing may preferably be of a female luer connector type according small bore connectors for liquid and gases in healthcare applications, as defined in ISO standards found in ISO594 and ISO80369 or similar, defining standards for small-bore connectors that contains a conical mating surface with a 6% (luer) taper intended for use in intravascular or hypodermic applications of medical devices and related accessories. In some embodiments, the female connector according to the inventive concept may be implemented as a luer slip connector (luer connector without a lock) or as a luer lock connector (luer connector containing a locking mechanism).

An advantage of the inventive concept is that the housing of the female connector may be formed without any protrusions that would hinder an outer frusto-conical sealing surface of a male luer cone of a male connector from mating with the frusto-conical female sealing surface of the inner cavity of the female connector housing, as required in the above-mentioned ISO standards. In contrast, in a female connector designed according to the prior-art publication US 2016/0235961 A1 mentioned above, the design of the entrance opening of the female housing with a radially inward protrusion prevents any a male connector from coming into such sealing contact with the inner housing wall along a frusto-conical minimum length of engagement to achieve a tight seal. According to the inventive concept, the frusto-conical female sealing surface of the housing may extend proximally all the way to the entrance opening of the housing, or it may as an alternative extend proximally only to a position at distance from the entrance opening of the housing.

A second advantage of the inventive concept is that the longer the length of engagement is, the greater the area of engagement is. The greater area creates a greater friction fit. Prior-art as well as the inventive concept has an axial force in the proximal direction resulting from compression of the elastomeric element in the distal direction. This force re-sets the elastomeric element to a closed position. However, it can also lead to an unsealed connection if the friction fit is not large enough. With an increased friction fit, the proximal direction force is counteracted to a greater extent than prior-art solutions, and helps to maintain a tight seal. As a result, the inventive concept makes it possible to accept higher axial loads from elastomeric compression, and/or to have more margin to an unsealed connection.

A further advantage of the inventive concept is that the female connector housing has an open distal end, and that the plunger is formed (manufactured) as a separate member from the female connector housing. Stated differently, according to the inventive concept the plunger is not made in one piece with the female connector housing. In contrast, the plunger of the female connector disclosed in US 2016/0235961 A1 is molded in one piece with the housing, resulting in a housing with a closed distal bottom. The features of the present inventive concept in this regard have the manufacturing advantage that a one-sided molding process is possible from the entrance (proximal) side of the housing. In the prior art, injection molding the plunger and the female inlet requires access from both sides (proximal and distal). This manufacturing advantage of the inventive concept is an especially important advantage in cases where a medical stopcock valve or the like is to be molded in one piece with multiple female connectors of the closed-system type. In such implementations, prior-art solutions for closed-system type female connectors requiring two-sided injection molding are not possible to use. The inventive concept allowing single-sided molding from the entrance side only makes such implementation possible. Especially, the inventive concept allows not only the flexible valve member but also the plunger to be fitted into the female connector housing after it has been molded.

A still further advantage of the inventive concept relates to the plunger. The inventive concept allows the plunger to have an outer surface which is relatively parallel to the inner surface forming the inner passage of the plunger, where both surfaces may have a decreasing diameter in the proximal direction. There are several benefits of having relatively parallel or at least same direction of draft. The diameter of the proximal end of the plunger must be less than the male luer passage. Meanwhile, the plunger should preferably have a passage through the plunger with a diameter as large as possible to allow as much flow as possible. Also, the plunger should preferably have an enclosing structure around its passage that is rigid enough, which requires a sufficient wall thickness. Prior-art solutions cannot be formed from one side only with draft with decreased diameter in a proximal direction.

In preferred embodiments, at least a part of the flexible valve member is compressible at least in a distal direction to assume its flow configuration in response to a male connector being connected to the female connector and engaging a proximal end of the flexible valve member. In such embodiments, when a male connector is being connected to the female connector, a distal tubular male part of the male connector may be inserted in a distal direction through the entrance opening of the inner cavity and may engage (i.e. be brought in contact with) a proximal end of the flexible valve member. As the male part is being inserted, it will push a proximal flow closing part of the flexible valve member towards the plunger, whereby the plunger will open the valve closing part of the flexible valve member creating an open flow path through the plunger, allowing a fluid flow through the interconnected male and female connectors. Before the male part is inserted, the proximal end of the flexible valve member will form a closure of the entrance opening of the housing.

According to the inventive concept, the flexible valve member at a distal end thereof presents a distal sealing part which is in sealing engagement with a distal part of the inner surface of the housing. The distal sealing part of the flexible valve member is designed to prevent fluid flow between the housing and a distal part of the plunger, such that any fluid flow through the female connector must go via the inner fluid channel of the plunger. This distal sealing part of the flexible valve member maintains the plunger positioned in relation to the housing. It may act as a distal stop element during the insertion of the valve member into the housing, defining a final mounting position of the flexible valve member, and optimally also a final mounting position of the plunger inside the housing. In use of the female connector, when the flexible valve member is deformed and moves from its flow stop configuration to its open flow configuration, the distal sealing part of the valve member may be essentially stationary relative to the housing and the plunger, while other parts of the flexible valve member may move in a distal direction relative the housing and the plunger during the opening movement.

In some embodiments, the flexible valve member may be of self-sealing type, structured and arranged to elastically expand and re-assume its flow stop configuration in response to the male connector being disconnected from the female connector. The return movement of the flexible valve member to its flow stop configuration may be obtained by an axial expansion of the flexible valve member, but also assisted by a radial expansion of the flexible valve member in embodiments having a frusto-conical interface between the plunger outside and the valve member inside sliding along the plunger. In such embodiments, parts of the flexible valve member located radially outside the plunger may be radially compressed during the opening movement, resulting in a corresponding return force during the re-closing movement. In other embodiments, the flexible valve member may be a non-self-sealing type valve member, structured and arranged to only open from an initial closed configuration, but not to return to a closed position.

In some embodiments, the plunger and the flexible valve member may together form an insert unit configured and sized to be insertable as one single unit through the entrance opening and into the inner cavity of the female connector. In other embodiments, the separate plunger may be inserted first into the female housing in a first insertion step, and the separate valve member thereafter inserted into the female housing as a second insertion step.

Embodiments where the plunger and the flexible valve member together form a single insert unit adds a further substantial advantage from a manufacturing perspective. The molding of the two parts may be simplified, and the insertion thereof may be simplified. In some embodiments, the plunger and the flexible valve member may be formed by a two-component injection molding technique, also referred to as 2K injection molding technique, or just 2K molding. One benefit is that the insert unit may consist of two different materials. A first material may be used for forming the plunger, such as a relatively rigid or semi-rigid plastic material, and a second less rigid material may be used for forming the flexible valve member, such as an elastomeric material like silicon rubber or the like. Especially, the two materials may differ in terms of their stiffness, at least in the axial direction. An additional advantage obtained by forming the two parts a single insert unit is that the two combined parts are ready for use as a single insert unit, without any need to assemble the two components together, or any requirement to insert the two components one by one into the housing. Accordingly, both the molding process and the assembly process are enhanced.

Both in embodiments where the plunger and the flexible valve member are inserted as separate parts, and in embodiments where the plunger and the flexible valve member are manufactured as one single insert unit, for instance by a 2K process, at least a part of the flexible valve member should preferably be slidable in relation to the plunger in the distal direction, to allow at least a part of the flexible valve member to move in relation to the plunger to the open flow configuration.

The plunger may be essentially completely encapsulated by the flexible valve member, except for a distal end opening of an inner flow channel of the plunger. In other embodiments, the flexible valve member may cover the plunger only in part. In embodiments where the distal end of the plunger is radially surrounded by a distal end of the flexible valve member, the positioning of the plunger inside the inner cavity may be accomplished at least by said distal end of the flexible valve member. During the assembly, when the insert unit is being inserted into the female housing, the distal part of the flexible valve member may be brought into engagement with a converging part of the housing, thereby defining a final insertion position of the insert unit. In such embodiments, the design may be such that there is no direct contact between the plunger and the housing, only an indirect contact via part of the flexible valve member holding the plunger in position. Alternatively, the distal end of the flexible valve member may end at a proximal distance from the distal end of the plunger, wherein the distal end of the plunger may be in direct contact with the housing, and wherein the flexible valve member forms a seal between the housing and the plunger at a more proximal position than the plungers distal end.

In preferred embodiments, the flexible valve member and the plunger should be prevented from being disengaged from the housing. In some embodiments, this may be accomplished by providing the proximal part of the flexible valve member with an engagement part of increased cross section, and by providing the inner surface of the housing with a mating engagement groove or similar space for receiving the engagement part of the flexible valve member. During assembly, when the flexible valve member is inserted into the inner cavity, the engagement part of increased cross section may initially be radially compressed and, subsequently, radially and elastically expand into the engagement groove of the housing to define a final retained mounting position of the valve member in the housing. In such embodiments, no further means are needed to keep the flexible valve member from falling out, such as glue or the like. During operation of the female connector, when a male connector is connected to open the fluid valve, the male connector may push the proximal part of the flexible valve member in the distal direction whereby the engagement part of the flexible valve member may be radially compressed and, thereby, allowed to leave the engagement groove of the housing during the opening movement. During a possible return movement of the flexible valve member to its closed position, the engagement will be re-established, again preventing the flexible valve member from being disengaged from the housing.

The plunger is preferably designed, dimensioned and positioned in relation to the flexible valve member such that the latter will prevent the plunger from leaving the housing.

In preferred embodiments, the plunger and the flexible valve member are structured and designed such that they only have to be inserted in the distal direction during manufacture, with no need to control the rotational direction or position about the insertion axis. However, one or more axial grooves formed in the inner surface of the housing and/or in the plunger may be used to prevent the flexible valve member and/or the plunger from rotating about the axial direction in relation to the housing, or between the plunger and the flexible member. The mounting force is at least in the axial direction for a Luer slip configuration, and for Luer lock there is both axial and rotational direction.

According to a third aspect of the inventive concept, there is provided a medical stopcock, comprising a stopcock housing, a stopcock valve member being rotatably received in the stopcock housing, and one or more female connectors according to the inventive concept and arranged on an outside of the stopcock housing. Especially, the stopcock housing and the female connector housing of each one of said one or more female connectors may be integrally formed, such as being molded in one piece. The manufacturing advantage mentioned above relating to the possibility of single-side molding the female connectors from their proximal side makes it possible to manufacture such a stopcock valve housing with one or more radially extending closed-system type female connectors, since molding from the distal end would not be possible in such stopcock applications.

In a stopcock according to the third aspect of the invention provided with multiple female connectors, all of the female connectors may be of closed-system type designed according to the inventive concept. As an alternative, fewer or only one of the female connectors may be designed as closed-system type according to the inventive concept. In some embodiments, the female connectors may all have identical housings, but only some being provided with an inserted plunger and an inserted flexible valve member. Especially, each housing may be provided with an engagement groove in the inner surface adjacent the entrance opening. Female connectors operating as closed systems will have an inserted plunger, and an inserted flexible valve member in engagement with the engagement groove of the housing. The engagement grooves of open female connectors may be inactive, i.e. not used. Such embodiments have the advantage that all female connectors of a stopcock may be designed and manufactured identically, independently of whether a female connector should operate as an open female connector, or as a closed system type female connector.

As a non-limiting example, the inventive concept may be implemented in the type of medical stopcock disclosed in applicant's publication WO 2017/153362 A1.

According to a fourth aspect of the inventive concept, there is provided a medical connection assembly, comprising a medical female connector according to the inventive concept, and a male connector connected to the female connector, said male connector presenting a tubular insertion part being in an inserted position inside said frusto-conical part of the inner cavity of the female connector, wherein the tubular insertion part of the male connector presents an outer frusto-conical sealing surface being in sealing engagement with the frusto-conical sealing surface of the female connector, and wherein the proximal end of the plunger being received at least partly into the tubular insertion part of the male connector. In the connected state, the tubular insertion part of the male connector will have moved the flexible valve member into its flow configuration, and the plunger is received at least in part into the tubular insertion part of the male connector. In some embodiments, the tubular insertion part of the connected male connector may be spaced from the tubular plunger of the female connector, avoiding any need for any direct seal between the insertion part of the male connector and the outside of the plunger in the connected state.

BRIEF DESCRIPTION OF THE DRAWINGS

The inventive concept, some non-limiting preferred embodiments, and further advantages of the inventive concept will now be described with reference to the drawings in which:

FIGS. 10A to 10C show a medical T-shaped connector device comprising a female connector according to the inventive concept.

DETAILED DESCRIPTION OF PREFERRED EMBODIMENTS

Figure 1A:
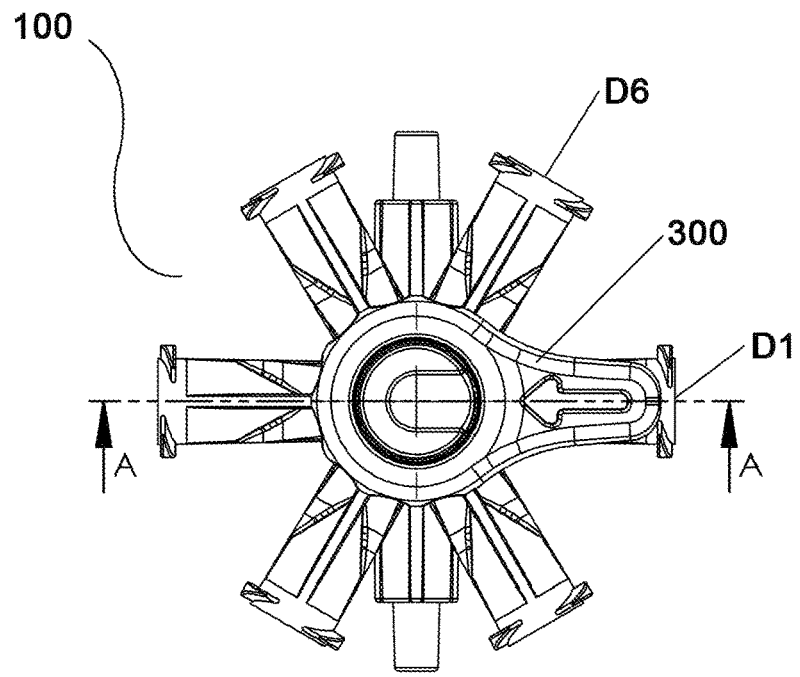
FIG. 1A is a top view of a first embodiment of a medical stopcock valve comprising a first embodiment of a medical female connector according to the inventive concept.
Figure 1B:
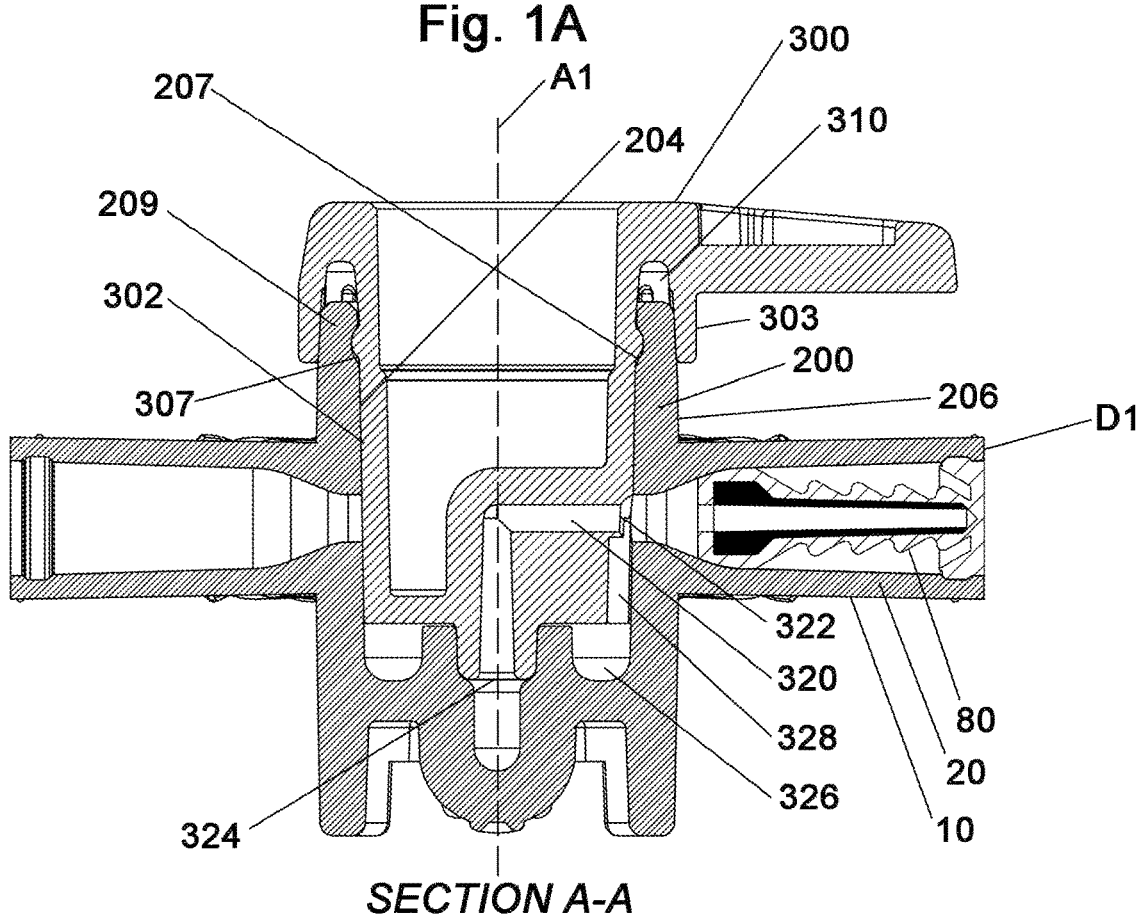
FIG. 1B is a cross-sectional view along line A-A in FIG. 1A.

FIGS. 1A and 1B illustrate an embodiment in which a female connector according to the inventive concept is implemented in a multi-inlet stopcock 100 of the kind disclosed in the above-mentioned publication WO 2017/153362 A1, the disclosure of which is hereby incorporated by reference. As an example, the stopcock 100 may be used for the administration of up to six different drug fluids, in combination with the administration of a neutral fluid, such as saline, between the drug administration. While the disclosed stopcock 100 comprises six rotational "drug positions", other embodiments may comprise a different number of positions. The stopcock 100 comprises a stopcock housing 200 shown in FIGS. 1C and 1D, and a rotary stopcock valve member 300. A cylindrical body of the stopcock valve member 300 is arranged in a cavity 205 of the stopcock housing 200 for rotation in relation to a rotational axis A1. The stopcock housing 200 may have a cylinder shape with constant radius, optionally presenting a minor draft, typically but not limited to about <1.5 degree for injection molding, alternatively a rotational symmetrical shape around the rotational axis A1 with variable radius.

A relatively mating outer cylindrical surface 302, alternatively a rotational symmetrical shape around rotational axis A1 with variable radius, of the stopcock valve member 300 is in sealing engagement with an inner surface 204 of the stopcock housing 200, thereby creating an assembly which is fluid tight and prevents fluid flow at areas where the surfaces are in sealing engagement. The radius of the outer surface 302 of the stopcock valve member 300 may be slightly larger than the radius of the inner surface 204 of the stopcock housing 200 in order to provide the sealed engagement.

For the assembly of the stopcock valve member 300 and the stopcock housing 200, an annular recess 207 is formed in the inner surface 204 of the stopcock housing 200 at a slightly tapered top part 209 thereof. A mating annular rim 307 is formed on outer side 302 of the cylindrical part of the stopcock valve member 300. At the same axial level, the stopcock valve member 300 presents a radially outer skirt 303 defining a downwardly open annular space 310. During assembly when the cylindrical part of the stopcock valve member 300 is inserted into the cavity 205 of the stopcock hosing 200, the tapered top part 209 of the housing 200 will be axially received in the annular space 310. Due to the radially protruding ring 307, the top part 209 will flex slightly outward, with an increased deflection with the axial distance when the valve member is axially mounted into place, which results in that the skirt 303 will flex slightly radially outward until the annular rim 307 is received in the annular recess 207 to maintain the stopcock valve member 300 in an axially fixed but still rotatable position in the stopcock housing 200. The valve 100 essentially has two locking mechanisms. One is the engagement between the annular rim and 307 and the annular recess 207. The other is the top part 209 exerting an outward force counteracted by an inward acting force of the skirt 303, where the largest forces in radial direction is just before the valve member 300 is in place, assisting to retain the valve member in its axial position and withstand a greater axial dislodgement force.

The stopcock housing 200 and the valve member 300 may be fabricated in any material which does not react chemically to any considerably extent with the drug fluids to be used, and which thereby and also in other aspects is suitable for medical applications. Moreover, the material must be suitable for sterile environments. Examples of materials include plastic materials. The plastic material may be transparent or opaque depending on the medical application. The stopcock housing 200 may be fabricated in the same material as the stopcock valve member 300. Alternatively, the stopcock housing 200 and the stopcock valve member 300 may be fabricated from different materials, such as materials of different stiffness. Different stiffness may be used for providing tactile feedback during operation of the valve. Different stiffness and different materials may also be used for providing improved sealing engagement.

Figure 1C:
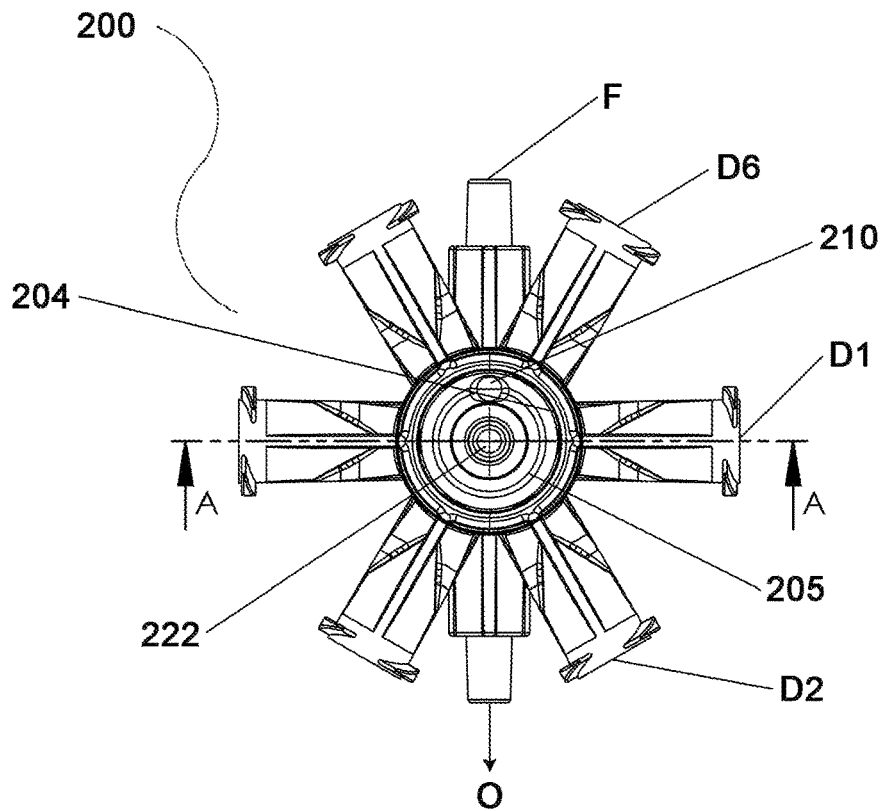
FIG. 1C is a top view of a stopcock housing of the stopcock valve in FIG. 1A.
Figure 1D:
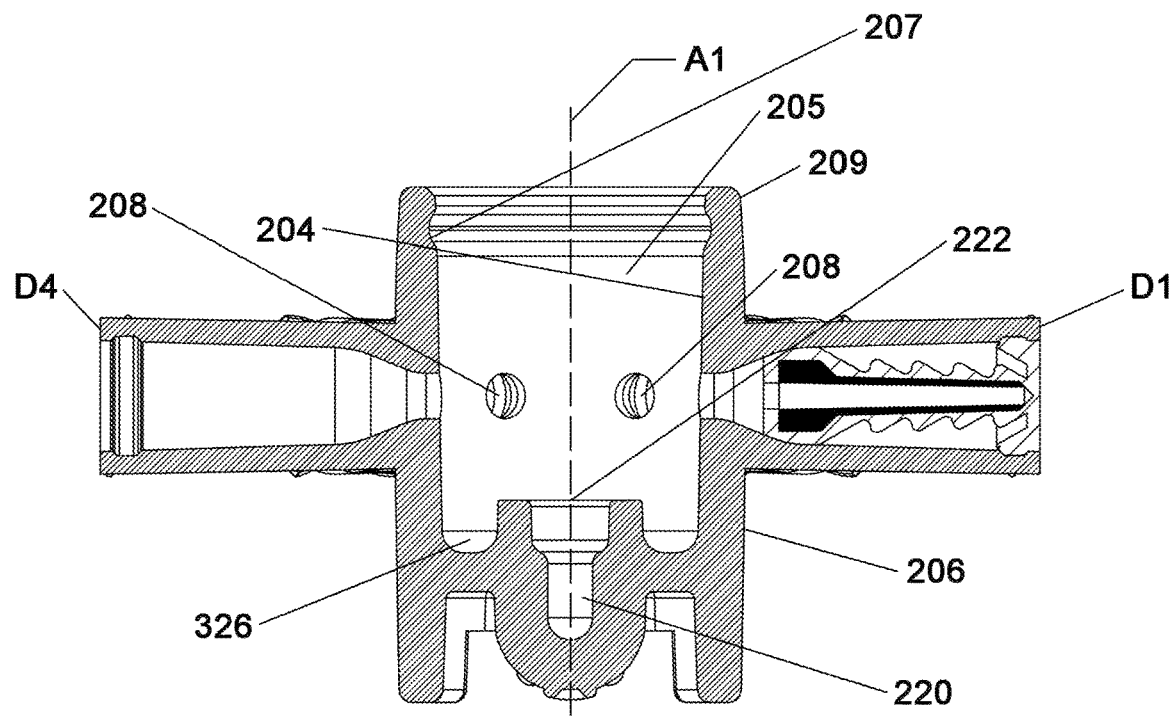
FIG. 1D is a cross-sectional view along line A-A in FIG. 1C.

As best seen in FIG. 1C, the stopcock valve 100 comprises a plurality of drug inlets D1 to D6, and a single flushing inlet F. In the illustrated embodiment, the flushing inlet F is arranged on a first axial level, and the six drug inlets D1 to D6 are arranged on a second different axial level with respect to the axis A1. Each one of the drug inlets D1 to D6 is fluidly connected to an associated drug outlet opening 208 which opens into the housing cavity 205. Each drug inlet D1 to D6 is formed by a female connector housing 20, which in this embodiment is integrally formed by molding with the cylindrical stopcock housing 200. The female connector housings 20 are preferably manufactured according to the above-mentioned luer ISO standards. In FIG. 1B, the female connector housing 20 of the first drug inlet D1 is provided with a valve insert unit 80, forming an embodiment of a female connector 10 according to the inventive concept. The female connector 10 is of so-called closed-system type, i.e. it is closed by the valve insert unit 80 until a male connector (not shown) is connected to the female connector 10. At that time, the female connector 10 is opened allowing fluid flow through the stopcock 100.

In FIG. 1B, only the first drug inlet D1 is shown as provided with a valve insert unit 80. In other embodiments, each one (or fewer) of the drug inlets D1 to D6 may be provided with its own valve insert unit 80 to form a closed-system female connector. A specific advantage of the present inventive concept is that all of the female connector housings 20 may be formed identically, regardless of whether a valve insert unit 80 is provided or not. Housings 20 with no insert unit 80 may operate as a conventional open-type female luer connectors.

As best seen in FIG. 1C, the flushing inlet F opens into the inner housing cavity 205 at a separate flushing outlet opening 210. As for the drug inlets D1 to D6, the flushing inlet F may also be integrally formed with the stopcock housing 200, and be shaped as a pipe or stud. In order to have access to the flushing fluid in each one of the drug positions, as will be described below, the flushing outlet opening 210 is located at a different axial level than the drug outlet openings 208.

The stopcock valve member 300 is provided with a main fluid passageway 320 in the form of an L-shaped tubular channel having an inlet 322 arranged at the outer cylindrical valve member surface 302 and an outlet 324 arranged coaxially with the axis A1 at the bottom of the stopcock valve member 300. Preferably, the inlet 322 and the outlet 324 constitute the only inlet and outlet, respectively, of the main passageway 320, in order to ensure a complete flushing thereof. In each selected drug position of the rotary stopcock valve member 300, the inlet opening 322 of the main passageway 320 is aligned with the associated outlet opening 208 in the stopcock housing 200.

As best seen in FIG. 1C, the stopcock 100 further comprises an outlet O which as an example may be connected, by a connection device (not shown) or glued or otherwise attached, to a downstream part of a primary IV line to be connected with a patient. In the present embodiment, the outlet O is formed in the housing 200. Specifically, the bottom part of the stopcock housing 200 may include an outlet O which is fluidly connected to the inner cavity 205 of the stopcock housing 200 by means of a bottom channel 220 having a central bottom outlet opening 222 positioned coaxially with the axis A1.

In use, a neutral fluid, such as a saline solution, may be led into the flushing inlet F by means of an upstream part of a main IV line. This neutral fluid, termed "flushing fluid", may comprise a sterile solution of sodium chloride (NaCl), or glucose, or other suitable flushing fluid that will act as a separator between the drugs connected to D1-D6. Due to the turn valve principle only one of the connected drugs in D1-D6 is flowing to the outlet at a time. The flushing fluid will flush residual drugs from the valve's internal volume and separate drugs downstream the valve. The flushing inlet F may be provided with a connection device (not shown) for connection with the flushing line or it may be glued or otherwise attached to the flushing line. Connection devices mentioned above for both the flushing inlet F and the outlet O may comprise male and female luer connectors. Other connector types may be used.

The stopcock 100 is designed according to the aforementioned publication WO 2017/153362 A1 such that in each selected drug position, the flushing inlet F is fluidly connected to the outlet opening 208 associated with the selected drug position. To this end, the stopcock 100 is provided with a distribution of the flushing fluid in a circumferential direction with respect to the axis A1. This is accomplished by means of a circumferentially oriented distribution channel 326 formed in the bottom of the stopcock housing 200. The flushing inlet F opens up in the distribution channel 326 at the flushing outlet opening 210 shown in FIG. 1C. The stopcock valve member 300 further comprises a transfer channel 328 for carrying the flushing fluid. The transfer channel 328 is fluidly connected to the distribution channel 326 and extends axially to the second axial level where the drug outlet openings 208 are located. When the valve member 300 is rotated, the main passageway 320 and the transfer channel 328 rotates together with the valve member 300. In the embodiment shown in FIGS. 1A and 1B, the inlet 322 of the main passageway 320 is always (i.e. in all rotational positions) in fluid connection with the flushing outlet opening 210 via the axial transfer channel 328 and the annular distribution channel 236. In contrast, this fluid connection may be blocked in certain rotational positions by a special implementation of the inventive concept as will be described later. For further details of the operation of this stopcock 100, reference is made to WO 2017/153362 A1.

$1^{st}$ Embodiment of the Inventive Concept

Reference is now made to FIGS. 1E, 2A and 2B, 3A to 3C, and 4 to 8, illustrating an embodiment of a female connector 10 according to the inventive concept, and a method for the manufacture thereof. As will be described below, a female connector 10 according to the inventive concept may be implemented in other types of medical devices than stopcocks.

The illustrated embodiment of the female connector 10 comprises as its main parts a housing 20, a tubular plunger 40, and a flexible valve member 60. In the illustrated embodiment, the plunger 40 and the flexible valve member 60 are manufactured as a single valve insert unit 80, to be inserted in one insertion step into the housing 20, preferably during the manufacturing. In alternative embodiments, the plunger 40 may be inserted first, and the flexible valve member 60 thereafter.

Figure 1E:
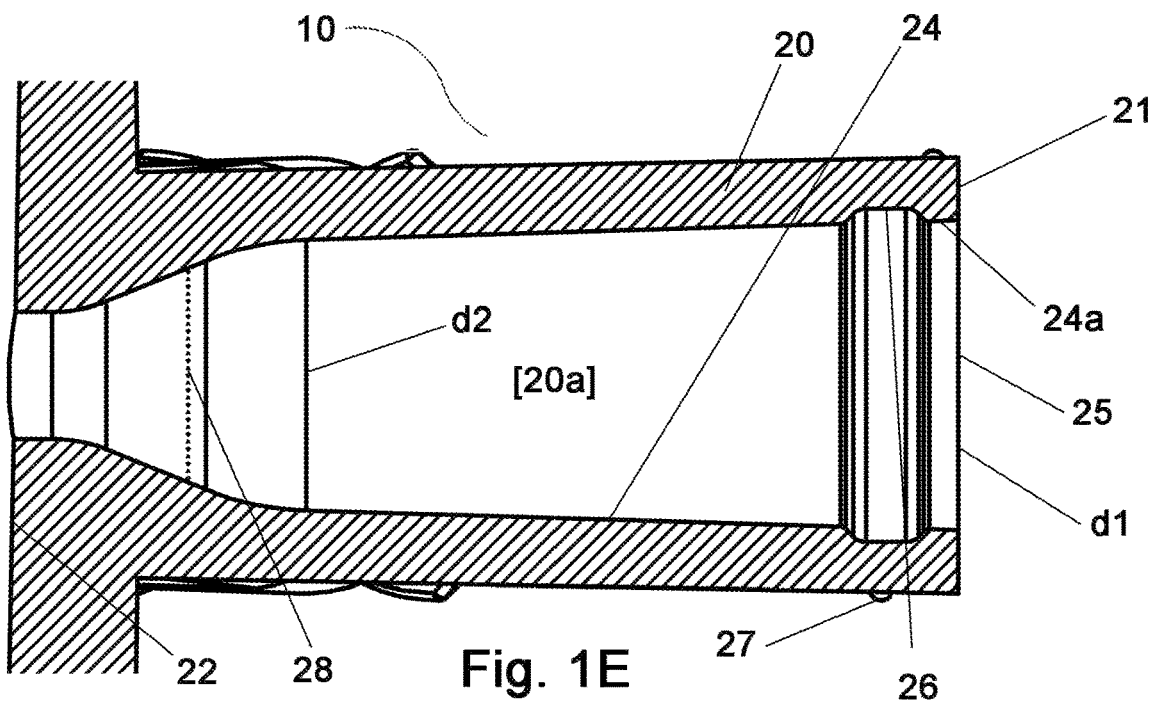
FIG. 1E is a cross-sectional view in larger scale of a female connector housing of the stopcock valve housing in FIG. 1C.
Figure 7:
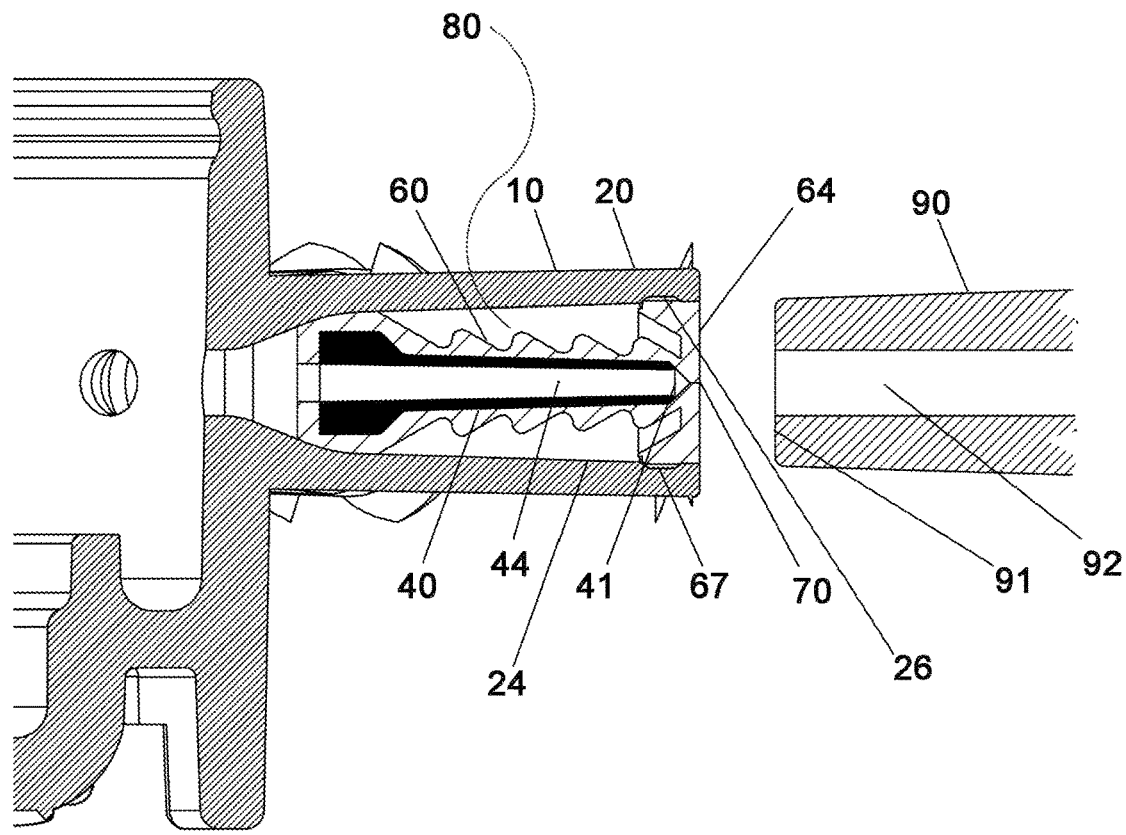
FIG. 7 is a cross-sectional view of a medical male connector.
Figure 8:
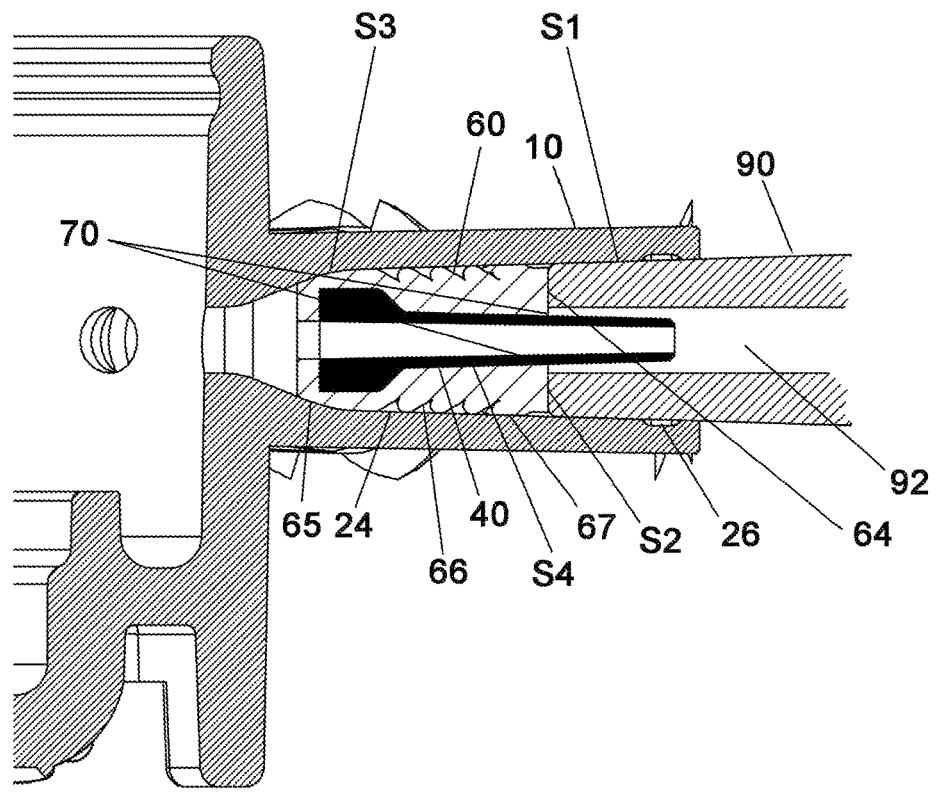
FIG. 8 is a cross-sectional view of an assembly of a male connector inserted into, and opening a female connector according to the inventive concept.
Figure 9A:
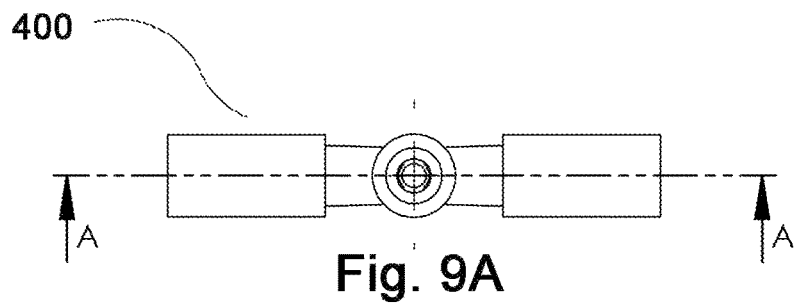
FIGS. 9A to 9D show a medical manifold comprising a plurality of female connectors according to the inventive concept.
Figure 9B:
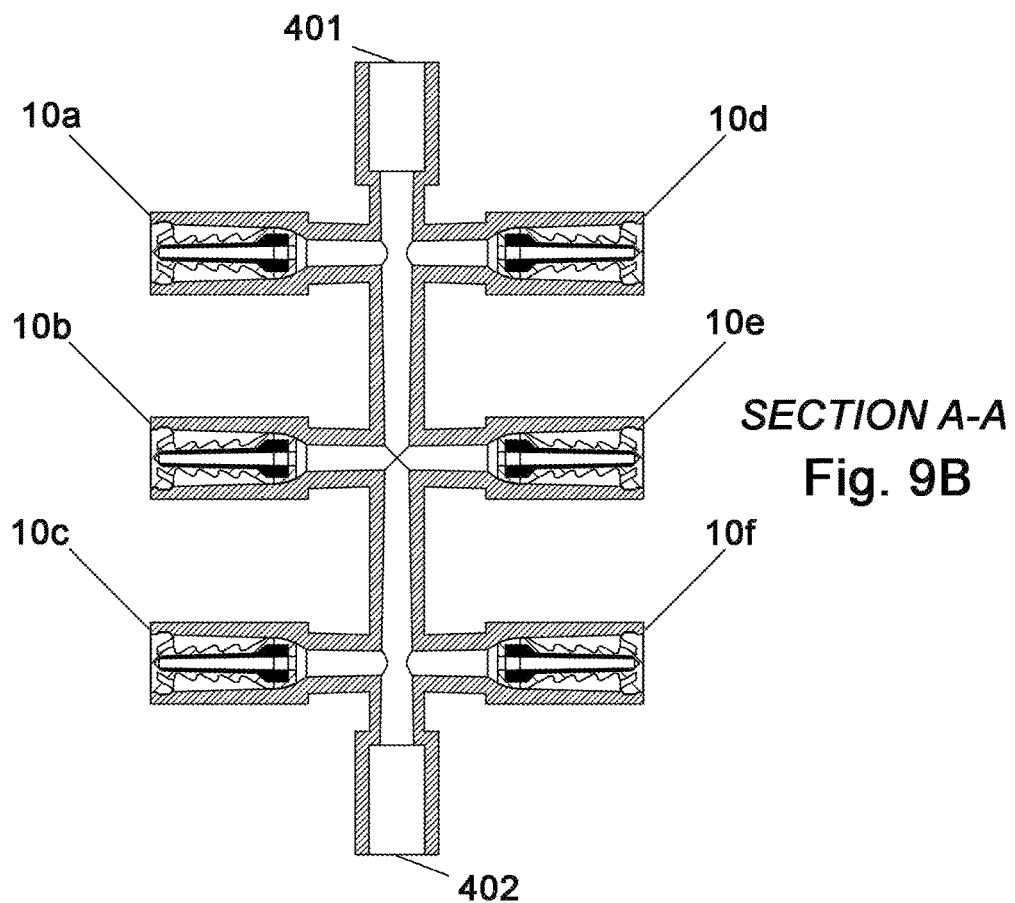
Figure 9C:
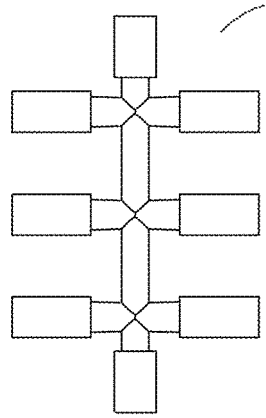
Figure 9D:
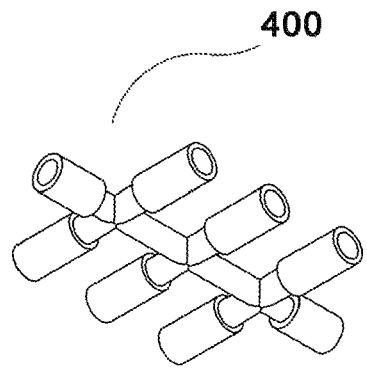

FIG. 1E illustrates the female connector housing 20. The housing 20 has an inner cavity 20a defined by an inner surface of the housing 20 and extending from an open proximal end 21 of the housing to an open distal end 22 of the housing 20. At least a part of the inner surface of the housing 20 forms a frusto-conical female sealing surface 24 arranged to seal with a conical sealing surface of a male connector (FIGS. 7 and 8). The frusto-conical sealing surface 24 has a maximum diameter d1 towards the proximal end 21 of the housing 20, and a minimum diameter d2 towards the distal end 22 of the housing 20. The proximal end 21 of the housing 20 presents an entrance opening 25 to the inner cavity 20a with a diameter equal to or larger than the maximum diameter d1 of the frusto-conical sealing surface 24. This allows the conical part of the male connector to be brought into sealing engagement with the frusto-conical female sealing surface 24. As mentioned above, the housing 20 may preferably be a luer housing manufactured according to the ISO standards mentioned above. In the illustrated embodiment, the frusto-conical sealing surface 24 extends proximally all the way to the proximal end 21 of the housing 20, which means that in this embodiment the maximum diameter d1 of the frusto-conical sealing surface 24 is equal to the diameter of the entrance opening 25. In alternative embodiments, the frusto-conical sealing surface 24 may extend to a position at a distance from the proximal end 21. In such alternative embodiments, the diameter of the entrance opening must still be equal to or larger than the maximum diameter d1 in order for the male-female seal to be established. As an example, the last proximal part may be cylindrical.

In FIG. 1E, there is further shown an annular engagement groove or undercut 26 formed in the inner surface of the housing 20, adjacent to but a distance from the entrance opening 25 of the housing 20. The engagement groove 26 extends radially outward from the inner frusto-conical surface 24 of the housing 20. Especially, it should be noted that the above-mentioned criteria—that the maximum diameter d1 of the frusto-conical sealing surface 24 is less or equal to the diameter of the entrance opening 25—still holds despite the formation of the engagement groove 26 which does not form part of the frusto-conical sealing surface 24. Further, an exterior threaded part 27 integrally formed with the housing 20 at the distal end 22 thereof allows a male connector to be locked to the female connector 10. The proximal part at a proximal distance from the engagement groove 26 may be rotational symmetric or form part of rotational symmetry, e.g. forming a half cylinder or otherwise formed so that an engagement groove still can act as a retainer for the insert 80 from axial dislodgement.

The line 28 in FIG. 1E represents the axial or distal position of the valve insert unit 80 when inserted into the housing 20. This position 28 is located at a converging distal portion of the housing 20. In the illustrated embodiment, the minimum diameter d2 of the frusto-conical female sealing surface 24 is larger or equal to any diameter of the inner cavity 20a between the female sealing surface 24 and the distal end 22 of the housing 20. As explained above, this design makes it possible to manufacture the housing 20 by a single-sided molding process, i.e. no access from the opposite distal side is required during the molding process. The molding may be done from the proximal side only. This is a substantial manufacturing advantage for manufacturing stopcocks with a plurality of closed-system type female connector housings 20, where prior-art closed system type female connectors are not possible to use because they require a two-sided molding process.

Figure 2A:
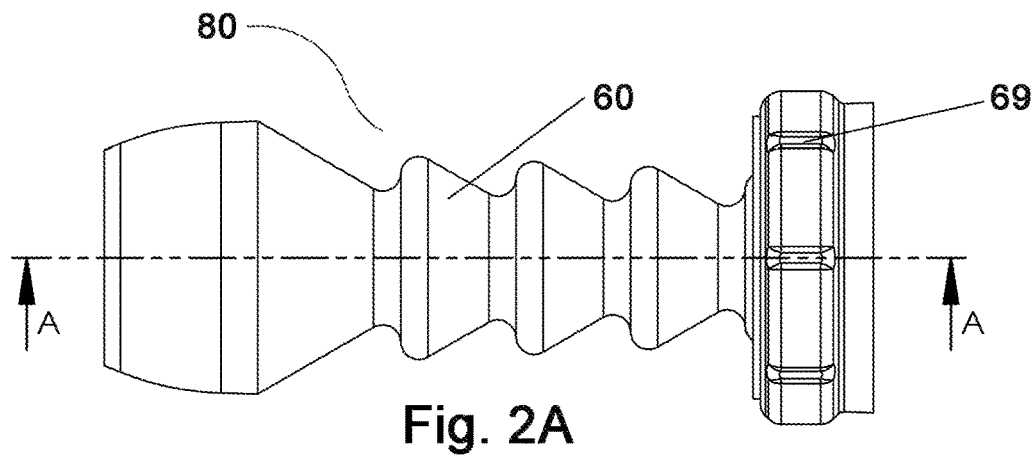
FIG. 2A is a side view of a first embodiment of an insert unit.
Figure 2B:
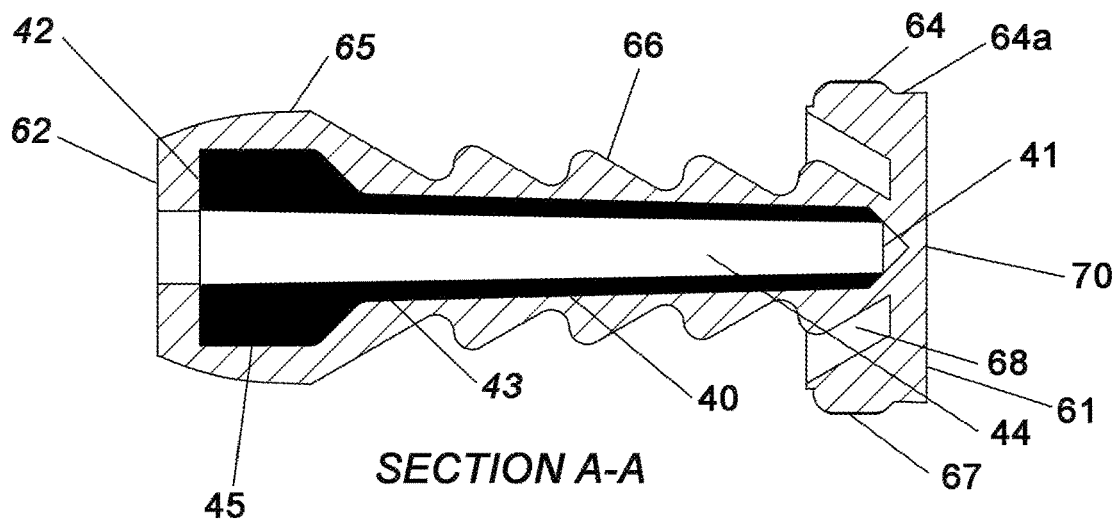
FIG. 2B is a cross-sectional view along line A-A in FIG. 2A.
Figure 3A:
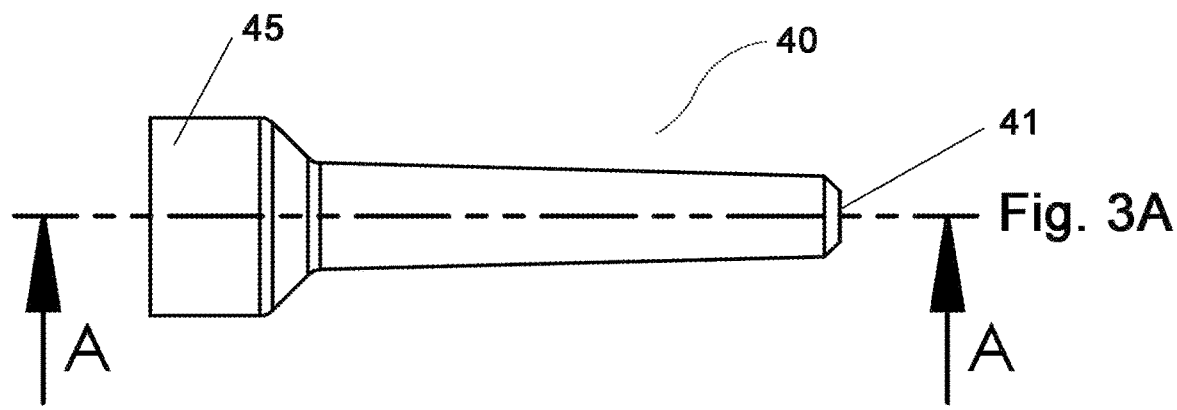
FIG. 3A to 3C show a plunger of the insert unit in FIG. 2A.
Figure 3B:
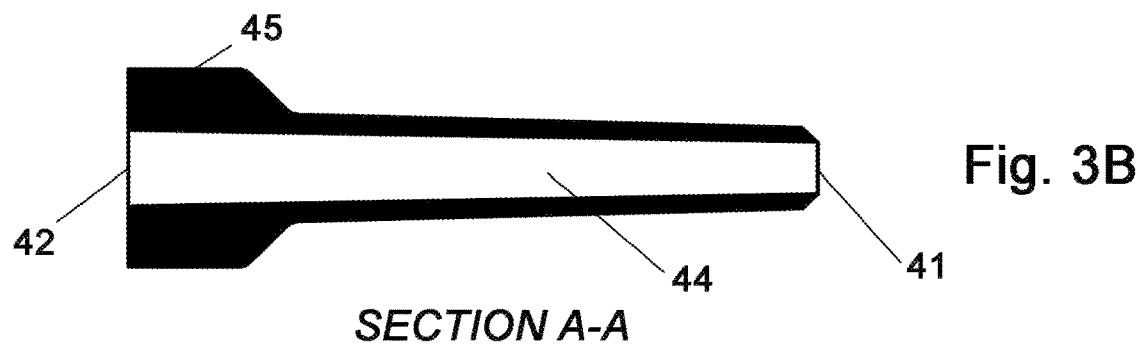
Figure 3C:
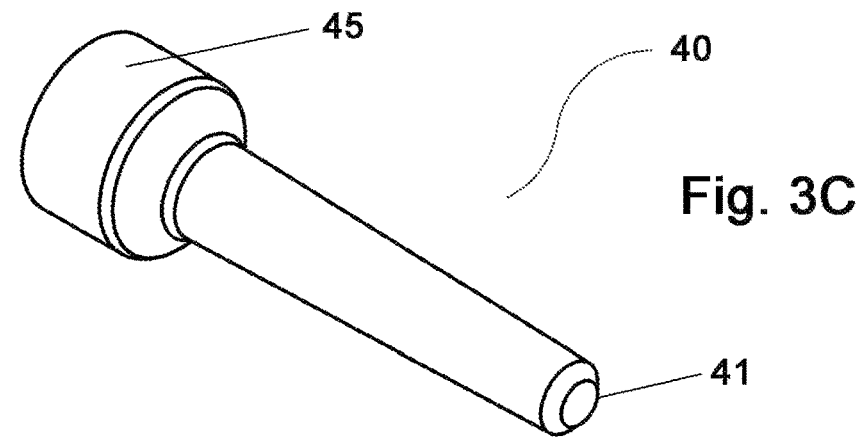
Figure 4:
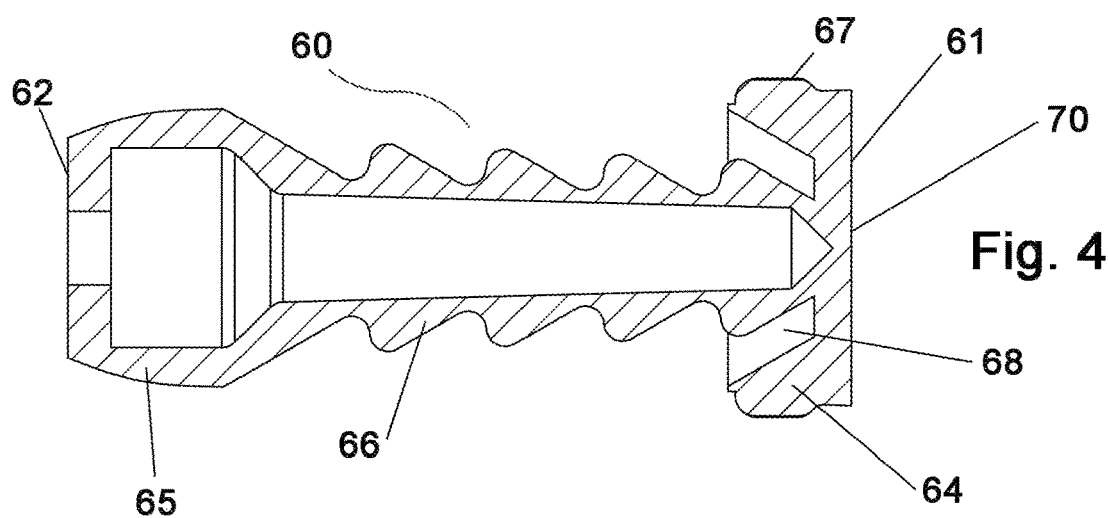
FIG. 4 is a cross-sectional view of a flexible valve member of the insert unit in FIG. 2A.

FIGS. 2A and 2B illustrate an embodiment of a valve insert unit 80, formed by a plunger 40 and a flexible valve member 60. The valve insert unit 80 is structured, sized, and arranged to be axially inserted into the inner cavity 20a of the housing 20 to form a final manufactured female connector 10. The insertion may be performed at the factory, or optionally later in connection with the use of the female connector 10. According to the inventive concept, both the plunger 40 and the flexible valve member 60 are manufactured as separate parts from the housing 20. Especially, the plunger 40 is not formed in one piece with the housing 20 as done in the prior-art solution described above. Again, this allows for the single-sided molding process. In the illustrated embodiment, the plunger 40 is substantially encapsulated by the flexible valve member 60, and embodiments of its manufacture will be discussed below.

In FIGS. 2A and 2B, the plunger 40 is a tubular member formed separately from the housing 20, and extends from an open proximal plunger end 41 to an open distal plunger end 42. The length of the plunger 40 is less than the length of the housing 20, such that it may be received entirely inside the inner housing cavity 20a. In the illustrated embodiment, the lateral outer cross-sectional dimension of the plunger 40 continuously increases in the distal direction. In this embodiment, the plunger 40 presents a frusto-conical outer surface 43 and an inner tubular fluid channel 44 extending all the way through the plunger from the open proximal plunger end 41 to the open distal plunger end 42. At its distal end 42, the plunger 40 presents a distal engagement part 45 presenting an increased cross section. The inner fluid channel 44 may be slightly tapered to facilitate the manufacturing thereof.

The flexible valve member 60 is formed from a flexible material, preferably an elastomeric material. Typically, the plunger 40 is formed from a material which is more rigid than the material for the valve member 60, at least in the axial direction. The valve member 60 extends from an initially closed proximal end 61 to an open distal end 62. From a functional aspect, the flexible valve member 60 has three parts: a proximal closure part 64, a distal sealing part 65, and a deformable intermediate part 66 which is located axially between and typically has a smaller diameter than the other two parts 64 and 65.

The proximal closure part 64 is the part of the flexible valve member 60 that acts as a closure of the plunger end 41 in the closed configuration of the female connector 10. The proximal closure part 64 has an outer diameter which substantially corresponds to the diameter of the entrance opening 25 of the housing 20, such that it may be positioned at the entrance opening 25 with a rather snug but still slidable fit with the inner surface of the housing 20. Axial movement should be possible. The proximal closure part 64 is provided with an annular rim 67 sized and configured to be brought into engagement with the engagement groove 26 of the housing 20 when the insert unit 80 is inserted into the housing 20, to prevent the insert unit 80 from falling out from the housing 20. During the insertion of the insert unit 80, the proximal closure part 64 of the valve member 60 is arranged to flex by elastomeric deformation in order for the engagement rim 67 to be engaged in the engagement groove 26 of the housing 20. Also, during use when the valve member 60 is pushed distally inwards by a male connector for opening of the female connector 10, a flexible deformation of the proximal closure part 64 will take place: deformation will take place so that the engagement rim 67 can leave the engagement grove 26, and deformation will also take place due to the tapered shape of the sealing surface 24. In some embodiments as the one illustrated, the proximal closure part 64 may be provided with one or more cavities 68 to facilitate such deformation. Thereby, the deformation will not only be a material compression, but also a bending and/or skewing deformation.

Further, the proximal closure part 64 in this embodiment is provided with a plurality of axially extending and circumferentially distributed vent grooves 69, the purpose of which will be described below. The illustrated embodiment of the proximal closure part 64 also presents a relatively short proximal annular part 64a, located proximally of the engagement rim 67. In the closed configuration shown, the annular part 64a mates with the minor part 24a of the frusto-conical sealing surface 24 which is located proximally of the engagement groove 26 (FIG. 1E). The surface 70 may be curved axially outwards or inwards or may essentially flat and parallel in relation to the proximal end 21 of the housing 20 to form a smooth surface to aid disinfecting the valve. If the proximal end 21 of the housing 20 has a chamfer edge or radius (not shown), the annular part 64*a* may be formed with an increase in diameter to mate with the chamfer or radius of the proximal end 21 of the housing 20.

Figure 6:
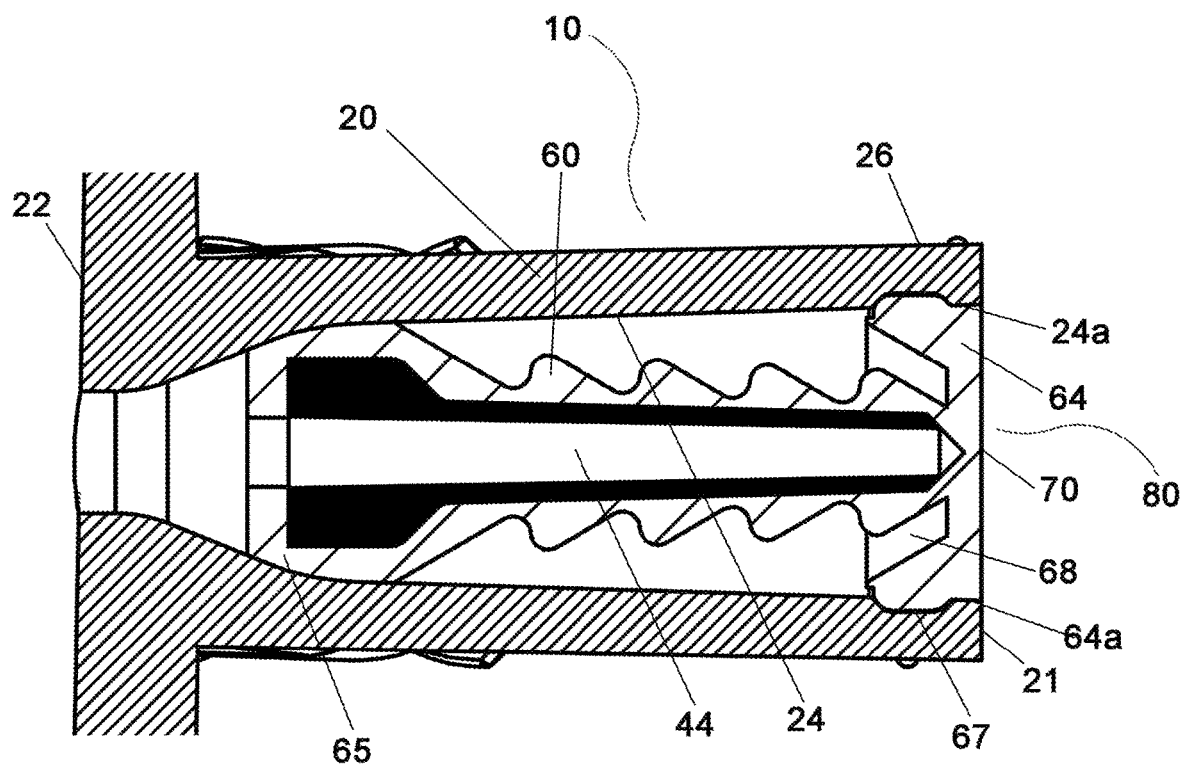
FIG. 6 shows the finally manufactured female connector in FIGS. 1B and 1D in larger scale.

In the closed position of the inventive female connector 10 shown in FIG. 6, the flexible valve member 60 assumes its flow stop configuration. In the flow stop configuration, the proximal closure part 64 is partly located proximally of the open proximal end 41 of the plunger 40 to form a fluid seal at the proximal plunger end 41, preventing fluid flow through the inner fluid channel 44 of the plunger 40. In the open position of the inventive female connector 10, the flexible valve member 60 assumes its deformed flow configuration where the proximal closure part 64 is pushed distally by the male connector against the plunger 40, whereby the proximal closure part 64 is deformed by the plunger 40 to allow a fluid flow into the open proximal plunger end 41, and through the inner plunger channel 44 and out of the distal housing end 22. In some applications, the fluid flow direction may be the opposite. In embodiments where the flexible valve member 60 is of re-closable type, the proximal closure part 64 may be provided with a pre-formed slit 70, a weakening, or the like, which extends through the proximal closure part 64. The slit 70 is closed in the flow stop configuration and opens (by the plunger 40) in the flow configuration. Other embodiments may be manufactured without any pre-formed slit or opening, where the proximal closure part 64 will instead be penetrated and locally ruptured by the plunger 40 in the open flow configuration.

Figure 5:
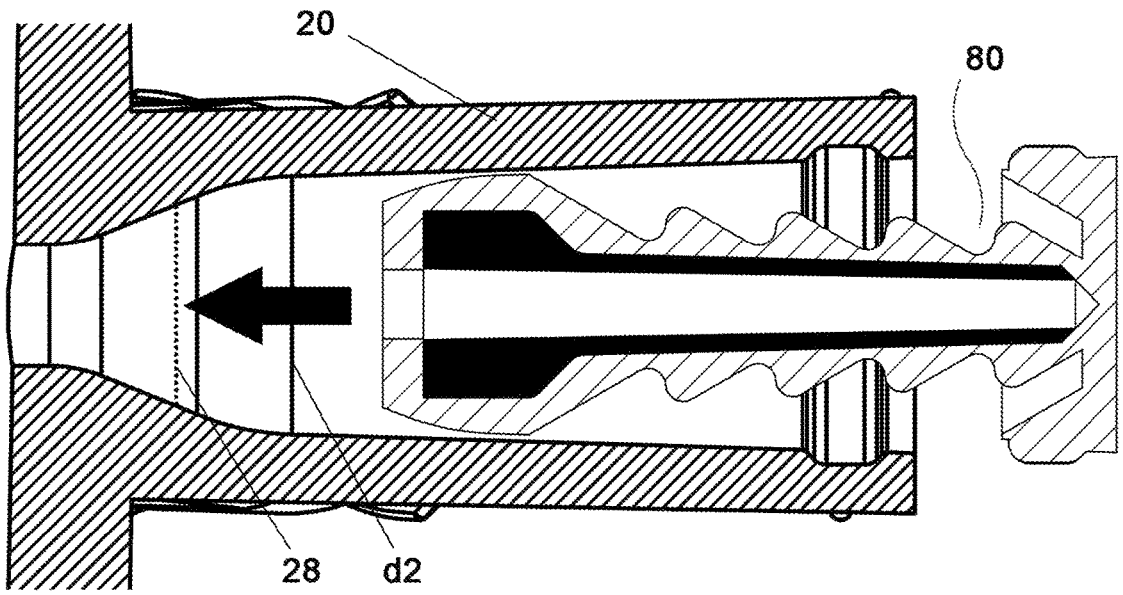
FIG. 5 illustrates a step in the manufacturing of the female connector shown in FIGS. 1B and 1D.

In the illustrated embodiment, the distal sealing part 65 of the flexible valve member 60 encloses the entire distal part 45 of the plunger 40, except for the distal opening thereof, allowing fluid flow at the distal end of the insert unit 80. The dimensions in the illustrated embodiment (FIGS. 5 and 6) are selected such that, when the insert unit 80 has been inserted into the housing 20 to its final distal position 28, the distal sealing part 65 of the flexible valve member 60 forms a fluid seal with the inner surface of the housing 20. In the illustrated embodiment, this fluid seal extends axially from a distal part of the frusto-conical sealing surface 24 to the distal position 28. This fluid seal prevents any fluid flow to the open distal end 22 via space between the housing 20 and the plunger 40. In the illustrated embodiment, the distal sealing part 65 of the flexible valve member 60 has additional functions. One [A1] such additional function is that it maintains the plunger 40 positioned in relation to the housing 20. In use, the sealing part 65 and the plunger 40 are substantially stationary in relation to the housing 20, however with a minor axial movement and possibly a rotational movement could occur when the male connector is connected. If a Luer slip connection is used then it is not necessary with rotational force exerted on the insert 80, but for a Luer Lock connection both an axial and a rotational force is probably exerted on the insert 80 due to the mounting forces of the male luer. Another such additional function of the distal sealing part 65 is that it defines a final insertion stop when inserting the insert unit 80 (FIG. 5). During the insertion, after the distal sealing part 65 has reached the final position 28 in the housing 20, the proximal closure part 64 may be inserted distally a bit further to engage with the engagement groove 26, resulting in a slight deformation of the intermediate part 66 of the valve member 60 and also a more effective seal at the distal sealing part 65. Yet another additional function with a relatively stationary seal 65 is that fluid that is downstream towards patient is not displaced in the distal direction or the proximal direction when connecting and disconnecting, which creates a neutral displacement closed system connector.

It may also be noted that alternative embodiments of the flexible valve member 60 may extend even further in the distal direction, including parts extending distally beyond the distal end 22 of the housing. Such an embodiment will be described later, where such further distal part may be used for establishing a secondary valve function.

In alternative embodiments, the distal part 45 of the plunger 40 may not be entirely enclosed by the flexible material of the flexible valve member 60. For instance, in a rotation-preventing design, the plunger 40 may be provided with distal legs or the like, extending radially towards the housing wall and engaging for instance axial grooves or openings therein. Such legs may prevent unwanted rotation of the insert unit 80 inside the housing 80 and may be designed and located such that they do not interfere with distal seal between sealing part 65 and the housing 20.

In alternative embodiments, it may also be envisaged to implement this seal in other ways. Especially, the seal may be located more towards the proximal side at a location where the flexible valve member 60 is moving axially in relation to the housing 20 when the female connector 10 is opened. One such alternative would be to provide a slidable seal between the proximal closure part 64 and the inner surface of the housing 20, without providing the vent grooves 69 which would destroy such a seal. However, a slidable seal may be more difficult to manufacture and more likely to leak. Such a movable seal would also be negative with large displacement of fluid in the distal direction when connected and in the proximal direction when disconnected.

In all of the discussed embodiments, it will be noted that the flexible valve member 60 has a dual sealing function. It seals or blocks (by its proximal part 64) the open proximal plunger end 41 in the closed position of the female connector 10, preventing fluid flow in plunger channel 44, and it seals (by its distal sealing part 65 or some other part) against the housing 20, preventing fluid flow in the space between the housing 20 and the plunger 40.

In alternative embodiments, the flexible valve member 60 may be implemented as a two-part, or multi-part, valve member. For instance, a separate first part may be configured to establish the proximal sealing function, and a separate distal part may be configured to establish the distal sealing function.

Manufacturing Aspects

The plunger 40 and the flexible valve member 60 may be formed by a multi-material injection molding (MMM) technique, especially by 2-component injection molding, also referred to as 2K injection molding, or just 2K molding. By such a process, the entire insert unit 80 may be manufactured as one single unit from two or more different materials in one molding process. The material type for forming plunger 40 may be a relatively rigid or semi-rigid plastic material. The second material type for forming the flexible valve member 60 may be an elastomeric material, which should preferably be less rigid than the first material at least in the axial direction. An elastomeric material is preferred in re-closable implementations. In alternative embodiments, the plunger 40 and the flexible valve member 60 may be formed separately, and thereafter optionally bonded together or assembled in other way to form a single insert unit 80.

The insert unit 80 will typically be inserted into the housing 80 during the manufacturing to form a complete female connector 10 of closed-system type. Alternative uses include providing the insert unit 80 as a stand-alone unit to be fitted into existing female (luer) connectors by the user With respect to the manufacturing of the plunger 40, the inner passage 44 of the plunger 40 may be formed by a mold core 50 which together with a mold half will form a mold cavity. During the mold process, this mold cavity is filled with a suitable plastic material. The mold core 50 and the mold half will create a cavity that will form the plunger 40 by mating.

Figure 17A:
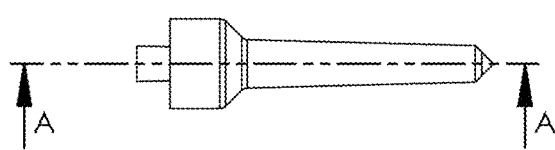
FIG. 17A to 17J illustrate a first embodiment of an insert unit, seen as an example of manufacturing by 2K molding.
Figure 17F:
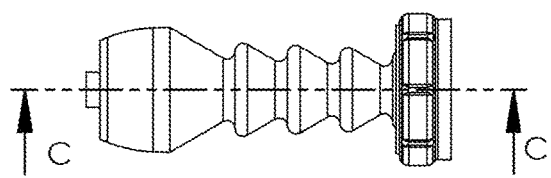
Figure 17B:
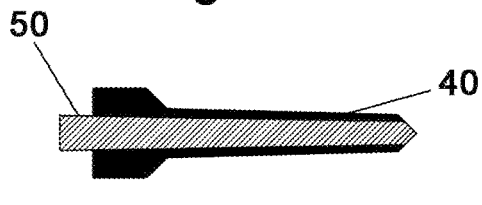
Figure 17G:
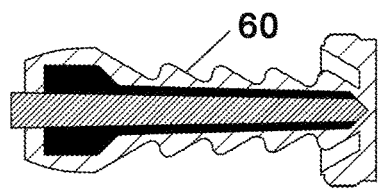
Figure 17C:
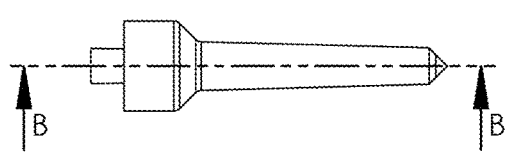
Figure 17H:
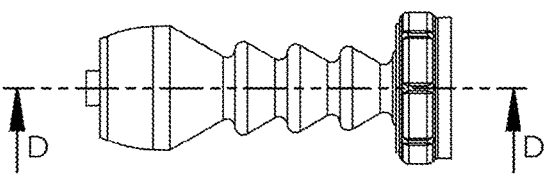
Figure 17D:
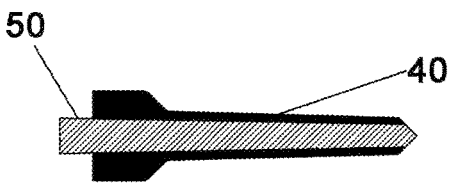
Figure 17I:
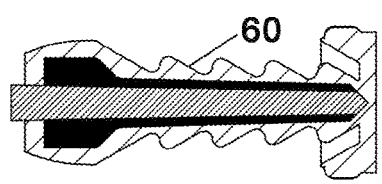
Figure 17E:
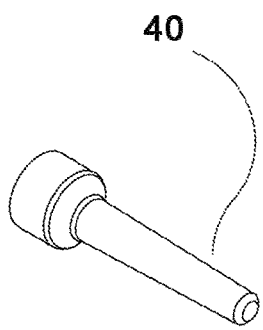
Figure 17J:
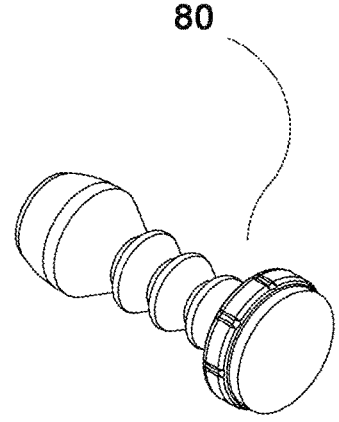
Figure 18A:
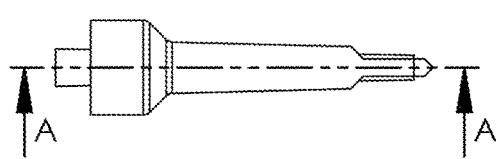
FIGS. 18A to 18J illustrate a second embodiment of an insert unit, seen as an example of manufacturing by 2K molding.
Figure 18F:
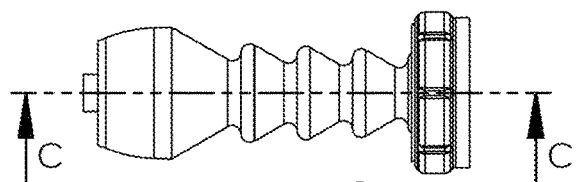
Figure 18B:
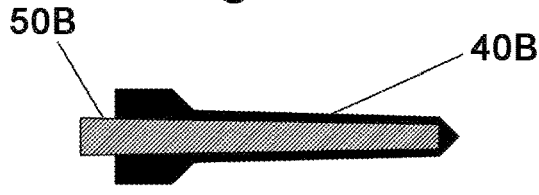
Figure 18G:
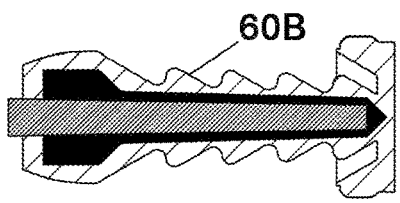
Figure 18C:
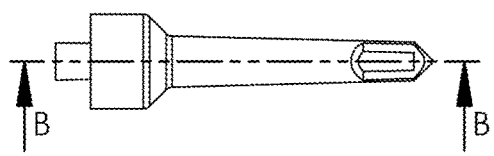
Figure 18H:
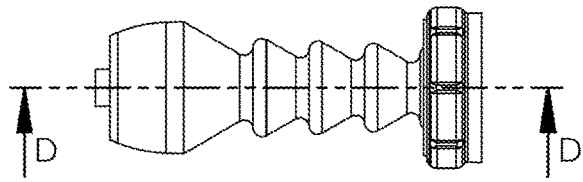
Figure 18D:
Figure 18I:
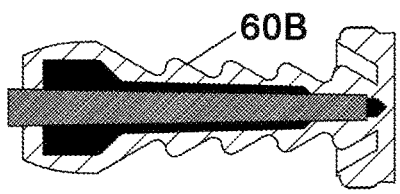
Figure 18E:
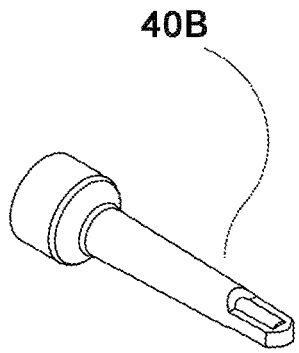
Figure 18J:
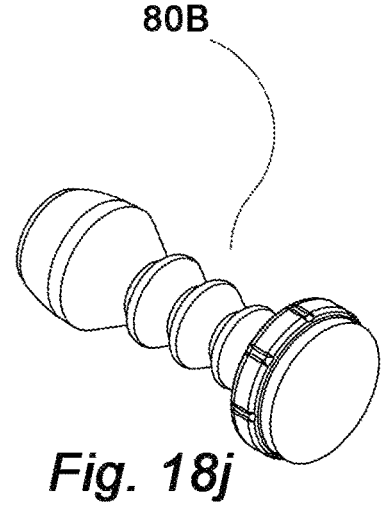
Figure 19A:
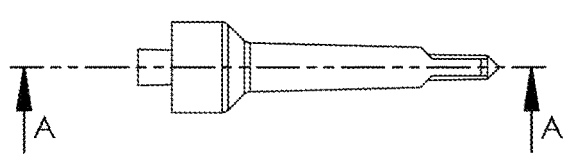
FIG. 19A to 19J illustrate a third embodiment of an insert unit, seen as an example of manufacturing by 2K molding.
Figure 19F:
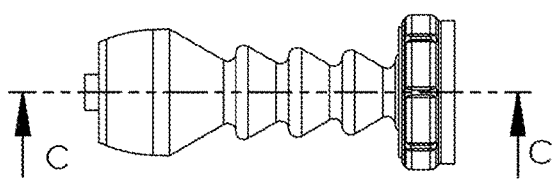
Figure 19B:
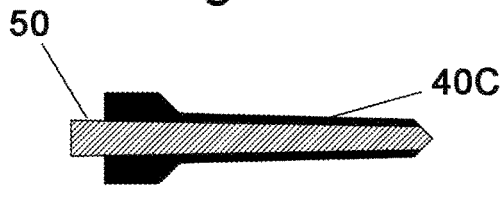
Figure 19G:
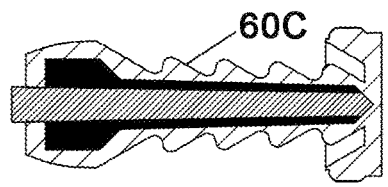
Figure 19C:
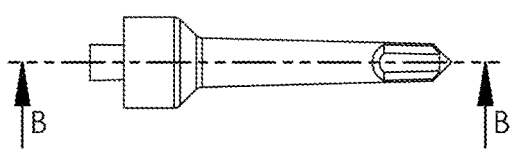
Figure 19H:
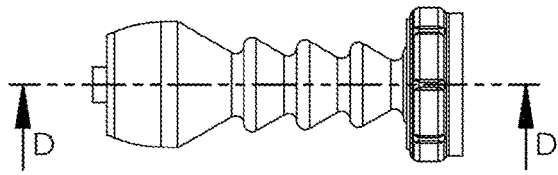
Figure 19D:
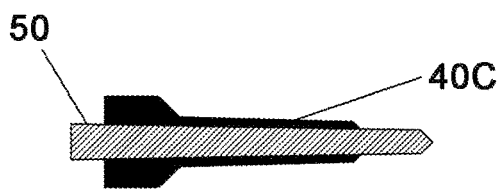
Figure 19I:
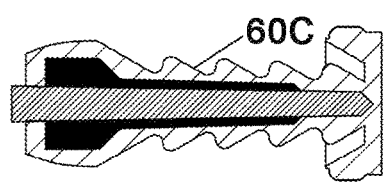
Figure 19E:
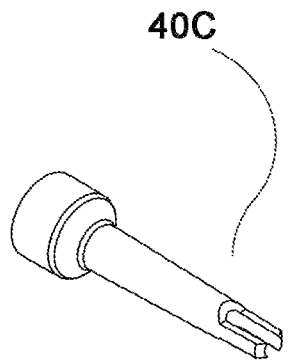
Figure 19J:
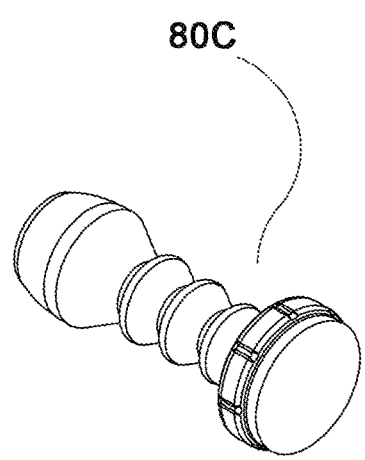

In the plunger embodiment described above, the axial fluid channel 44 of the plunger 40 opens co-axially at the proximal end 41 of the plunger 40, as best seen in FIGS. 17A to 17D. When molding such a plunger 40 with a co-axial proximal opening, the mold core 50 will mate with the mold half at the proximal plunger end 41. This will make the plastic to form circumferentially around the mold core 50 FIG. 17E shows the finished molded part 40.

In an alternative plunger embodiment 40B illustrated in FIGS. 18A to 18E, the proximal end 41 of the plunger 40B presents a lateral opening 48 open in two opposite lateral directions. In the open configuration, the plunger 40B may extend through the proximal closure part 64 to an extent sufficient to expose at least a part of the lateral opening 48 to allow fluid passage through the plunger channel 44. The mold core 50B is different than mold core 50 in this embodiment.

FIGS. 19A to 19E illustrate a still further plunger embodiment 40C being a combination the first and second embodiments 40 and 40B described above. In this embodiment 40C, the proximal end 41 of the plunger 40C has a proximal opening 49 which opens both co-axially and in the lateral directions. The mold core 50 may be designed exactly the same for forming the plunger 40, and 40C.

The flexible valve member 60 may present at least two different main configurations, using reference numerals 60 and 60', respectively. The second configuration 60' will be described later in the description.

With reference to FIGS. 17F to 17I, 18F to 18I, and 19F to 19I, if a 2K molding process is used, at the second stage of the 2K molding process, the (second) mold cavity is different from the first mold cavity. The core that forms the plunger's channel 44 and the now settled plastic from the first stage will form together a new combined core, which together with the second cavity is used to mold the flexible valve member 60, 60'. It should be noted that manufacturing the plunger 40C and 40 may be done using the same core design and same core tip design for both. What stated in the following for the first configuration 60 applies to the second configuration 60' as well.

It should also be noted that the internal shape of the flexible valve member 60 may have three different internal shapes due to the resulting different combined core and plunger 40, 40B and 40C described above. But the outside may be the same since it may be exact same cavity shaping the outside of valve member 60 in each embodiment. This results in embodiments 60, 60B, 60C.

The female housing 20 may be molded as a luer type inlet where frusto-conical sealing surface has a taper of about 1.72 degree in relation to the axis of symmetry. This conical shape is mating against a compatible male luer to be inserted inside the female luer. The male outer conical shape is mating with the female inside surface, and establishes a sealing surface in its mated position.

Means for holding the insert unit 80 maintained in the housing 20 may not interfere with the insertion process and the conical seal, and may thus not present any radially inward projecting parts. The engagement groove 26 formed in the inner surface of the housing 20 forms a solution to this requirement. The engagement groove 26 does not interfere with the insertion of the male luer, and it does not interfere or hinder the establishment of the conical seal. In the manufacturing process, the engagement groove 26 may be formed by an injection molding process where the inner surface of the housing 20 is formed by a mold core.

The housing 20 may be formed by one or more mold halves. The core forming the inner cavity 20a will create a radial elastic expansion of the housing 20 when the core will move axially outwards. This may create a compression of the plastic material toward the mold half, preventing movement of the core, at least not without damaging the formed housing. Therefore, it may be necessary to form a space between the housing 20 and the mold half before moving the core axially outwards When one mold is used to form the housing 20, that mold must axially separate from the newly formed housing part 20, to create space from the housing 20, before the inlet core can be moved from the housing 20.

When more than one mold is used to form the female inlet, the molds must be radially separated from the formed housing part 20 before the inlet core can be moved from the formed housing part 20.

The sequence described above, can be achieved with a delay of the inlet core movement in relation the movement of the mold halves. There are several ways to delay a core extraction.

One of these ways may be, that the angle hole diameter may be more than the diameter of the angled hole that is attached to or integrated with the inlet core. This will make it possible of one of the molds to separate from the housing 20 before the angled pin makes contact with the oversized hole in the inlet core.

The other mold half may move away from the formed housing part 20 before the movement of the inlet core, by the fact that the retainer plate that is attached or integrated to the inlet core has an interspace between the retainer plate and the mold half. This allows for a separation of the mold half from the formed housing part 20, before the mold half make contact with the retainer plate of the inlet core. When the retainer plate of the inlet core makes contact with the mold half and when the angled pin makes contact with the oversized hole in the inlet core, an axial movement of the inlet core will be created.

Operation

FIGS. 7 and 8 schematically illustrate the operation of the embodiment described above, where the female connector 10 is implemented in the stopcock 100.

FIG. 7 illustrates the closed or flow-stop configuration of the female connector 10, where the proximal closure part 64 of the valve member 60 acts as a closure of the plunger end 41. The proximal closure part 64 with its slit 70 closed is partly located proximally of the open proximal end 41 of the plunger 40 to form a fluid seal at the proximal plunger end 41, preventing fluid flow through the inner fluid channel 44 of the plunger 40. The annular rim 67 of the proximal closure part 64 is in engagement with the engagement groove 26 of the housing 20, preventing the insert unit 80 from falling out from the housing 20. A male connector 90 to be connected is also illustrated. The male connector 90 has a tapered luer tip with an insertion end surface 91, and an internal fluid channel 92. The taper of the male luer tip may preferably correspond to the taper of the female sealing surface 24.

FIG. 8 illustrates the open configuration, where the male connector 90 has been inserted into and connected to the female connector 10 to open the latter. The inventive configuration of the female connector 10 allows the tapered outer side of the male connector 90 to form a seal along a substantial axial length with the tapered inner sealing surface 24 of the female connector 10, as indicated at reference S1. This seal S1 forms the primary fluid seal of the connected assembly. In the open configuration in FIG. 8, the valve member 60 has been pushed distally inwards by the male connector 90 for opening the female connector 10. The insertion end surface 91 of the male connector 90 is in engagement with the proximal end surface of the valve member 60, forming a seal S2. During the axial insertion of the male connector 90, flexible deformations take place of the elastomeric valve member 60:

- The intermediate part 66 is axially compressed when sliding along the plunger 40. It should be noted that FIG. 8 is schematically drawn with respect to the shape of the compressed intermediate part 66. The compressed shape may differ from what shown in FIG. 8. The axial compression generates a bias used for an optional subsequent return movement.
- The proximal closure part 64 is deformed so that the engagement rim 67 can leave the engagement grove 26.
- The proximal closure part 64 is also deformed due to the tapered shape of the sealing surface 24.
- The proximal closure part 64 is deformed by the plunger 40 at the region of the slit 70 such that the slit 70 opens and the plunger 40 extends through the slit 70 and into the fluid channel 92 of the male connector, establishing an open fluid path through the connected assembly.
- The intermediate part 66 may also be radially deformed towards the plunger 40, optionally forming a fluid seal as indicated at reference S4. Such a radial deformation may be due to a tapered configuration of the outside of the plunger 40.
- The configuration of the distal sealing part 65 of the valve member 60 may be substantially unchanged compared with the situation in the closed position in FIG. 7. However, a slight compression may occur due to axial forces acting on the distal part 65. A seal between the distal sealing part 65 and the housing 20 is indicated at reference S3.
- To the extent that the distal sealing part 65 is substantially unchanged during the opening operation, the position of the plunger 40 inside the housing 10 will also be substantially unchanged.

In the illustrated embodiment, the dimensions are selected such that the seal engagement at S1 is established before the tapered plunger 40 is allowed to stop the insertion movement, by engaging the inner passage 92 of the male connector 90. This is illustrated in FIG. 8 by a small radial gap at the insertion end 91 between the outside of the plunger 40 and the male connector 90.

From the configuration in FIG. 8, the male connector 90 may optionally be disconnected from the female connector 10 to close the latter again. When the tip of the male connector 90 is withdrawn, the compressed valve member 60 will return to its closed position in FIG. 7 due to the bias forces generated by the compression.

A female connector 10 according to the inventive concept is preferably designed to avoid that its valve function acts as a positive displacement valve or as a negative displacement valve. A positive displacement valve has the drawback that a volume compression is created during valve opening, and a movement of fluid downstream the valve in a distal direction, which may lead to negative consequences such as air embolism and short-term boulous of the drugs inline below the valve. A negative displacement valve has the drawback that a movement of fluid downstream the valve in the proximal direction due to a suction force is created during valve closure, which may lead to negative consequences such as a likelihood for Catheter Related Blood Stream Infection (CRBSI). This situation is particularly critical if the valve is located close to the vascular system of the patient. The distal sealing part 65 of the flexible valve member 60 should therefore preferably be prevented from moving distally in relation to the housing 20 during valve opening, and be prevented from moving proximally in relation to the housing 20 during valve closure. For this reason, the engagement rim 67 of the proximal closure part 64 may be provided with the above-mentioned vent grooves 69 or similar vent means. The radial depth of the vent grooves 69 is preferably less than the radial thickness of the engagement rim 67, and/or less than the depth of the engagement groove 26 of the housing 20.

The vent grooves 69 serve to ventilate air from the space in the inner cavity 20a between the intermediate part 66 and the housing 20 when the flexible valve member 60 is moved and compressed axially upon valve opening. Thereby, less axial force is needed to connect the male connector, as the otherwise entrapped air would act as an air cushion with an increased counter-force in the proximal direction. Also, this design reduces the requirement to design a sealing at the distal part 65 that otherwise has to withstand displacement from the force of the compressed air pressure inside the cavity 21. The vent grooves 69 also serve to ventilate air into the inner cavity 20a when the flexible valve member 60 expands axially upon valve closure. Thereby, no suction force will act on the distal sealing part 65, preventing the later from moving proximally in relation to the housing 20, thereby preventing a negative valve displacement. As a result, a substantially neutral displacement valve function is obtained.

Implementation in Alternative Medical Devices

In the foregoing, the inventive concept has been disclosed as implemented in a multi-drug stopcock 100. In the following, a short description of alternative devices is presented. In order to avoid an extensive repetition, everything stated and shown with respect to the embodiment of the female connector 10 above applies also to the following alternative devices.

FIGS. 9A to 9D illustrate a multi-port infusion manifold 400 presenting six female connectors 10a to 10f with the same design as the female connector 10 in the previous embodiment, one central inlet 401, and one central outlet 402. The single inlet and single outlet are here shown as tubing connectors, but could be of a Luer type or by other connector type suitable to connect the manifold to an infusion line.

FIGS. 10A to 10C illustrate a Y-type infusion connector device 500, presenting one female connector 10 with valve function as describe above, one inlet 501 and one outlet 502. The single inlet and single outlet are here shown as tubing connectors, but could be of a Luer type or by other connector type suitable to connect the manifold to an infusion line.

Figure 11A:
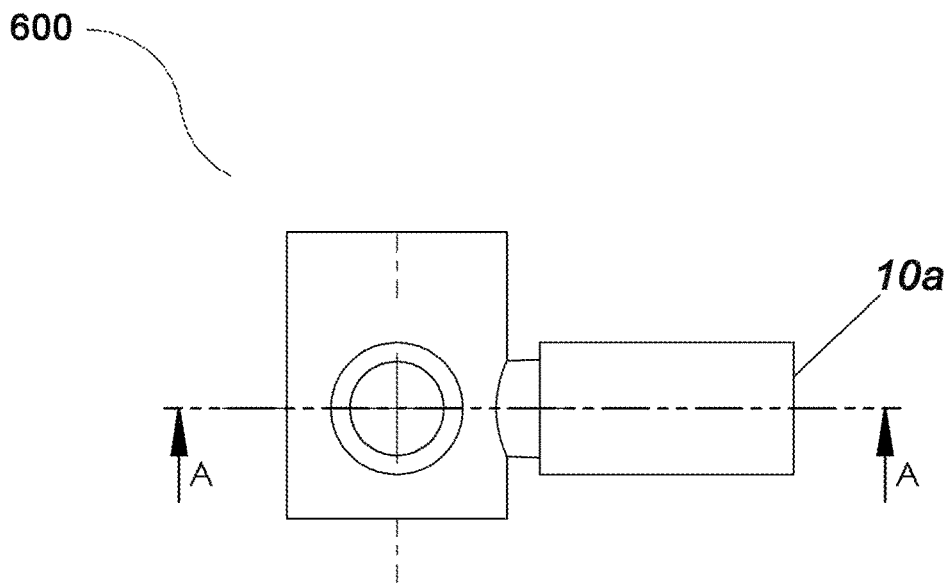
FIGS. 11A and 11B show a second embodiment of a stopcock housing of a medical stopcock comprising two female connectors according to an embodiment of the inventive concept.
Figure 11B:
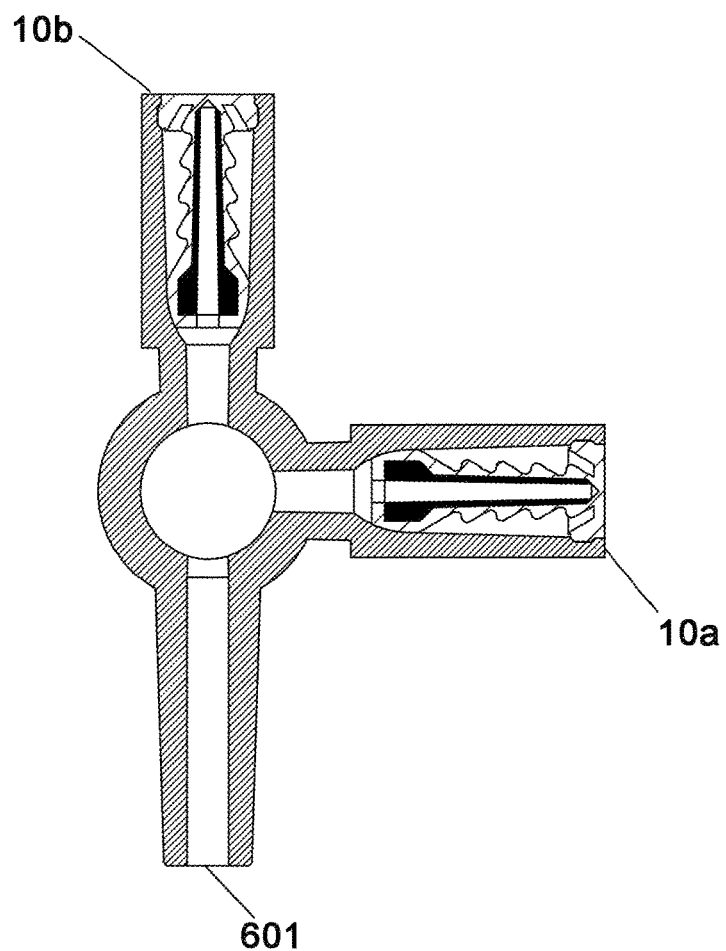
Figure 12A:
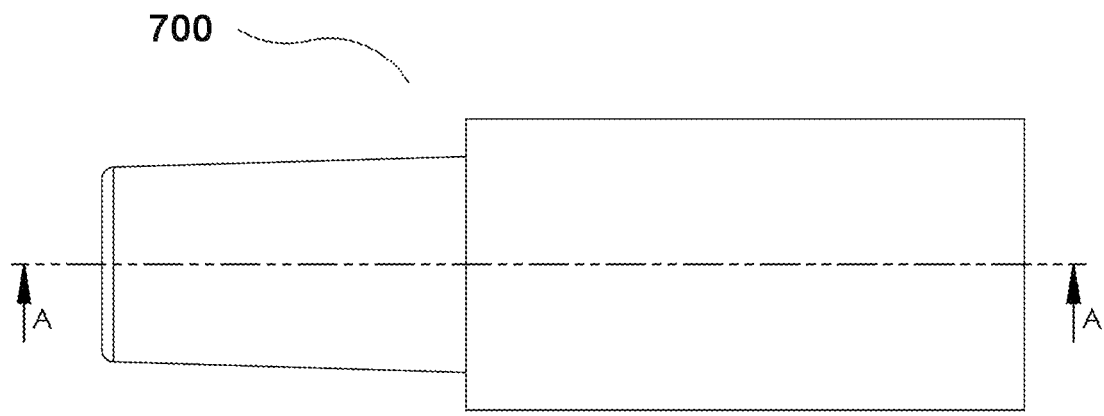
FIGS. 12A to 12C show a medical adapter comprising a female connector according to the inventive concept.
Figure 12B:
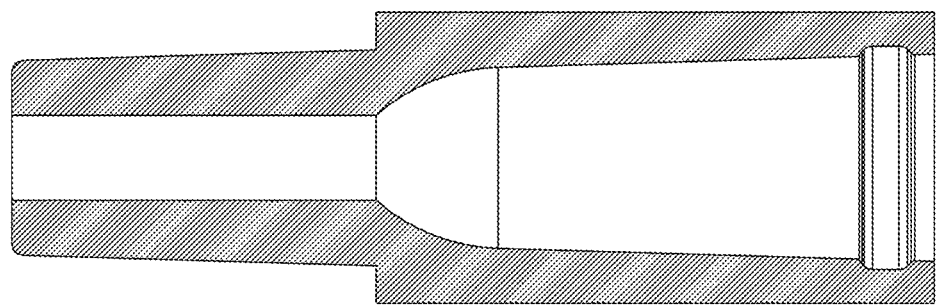
Figure 12C:
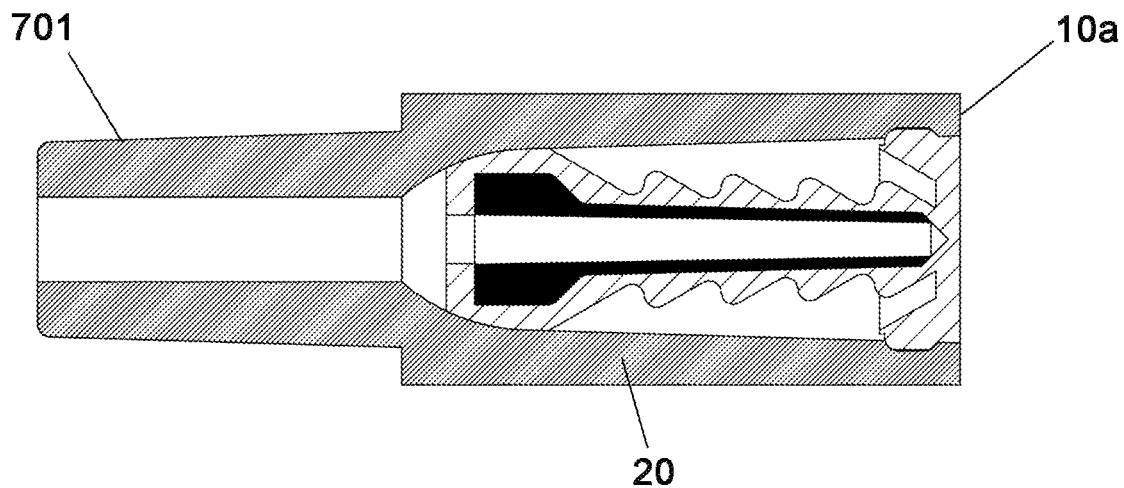

FIGS. 11A and 11B illustrate a housing 600 of a medical 3-way stopcock, having two inlets 10a and 10b, each formed as the female connector 10 in the previous embodiment, and one outlet 601. The outlet is here shown as a Luer slip type, but can be of any connector type suitable to be connected to an infusion line. The inlet 10*b* may instead be of any connector type suitable to be connected to an infusion line FIGS. 12A to 12C illustrate a medical adapter device 700 having a female side 10*a*, and a male side 701. The female side 10*a* is designed according to the female connector 10 in the previous embodiment. The housing 20 of the female side 10*a* is molded in one piece with the male side 701. The male side 701 may form a male luer cone. This device 700 may be inserted into an open-type female connector (not shown) to convert the same into a closed-type female connector with the inventive concept valve function.

Secondary Valve Function

Reference is now made to FIGS. 13, 14, 15A to 15D, and 16A to 16B, illustrating a modification of the stopcock 100 shown in FIGS. 1A to 1D, and FIGS. 7 and 8. Identical parts are identified with the same reference numerals. The modification lies in a distal extension of the flexible valve member 60, resulting in a modification of the fluid passageways inside the stopcock housing 200 as will be described below. In the modified stopcock 100', all other parts are identical with the corresponding parts in the previous embodiment 100, and all functions, advantages and alternatives apply to this embodiment 100' also. In short, by this modification it becomes possible to convert the stopcock 100 in FIGS. 1A to 1D, and FIGS. 7 and 8 from a stopcock where there always exists—especially in the drug positions—a fluid connection between the main passageway 320 of the stopcock valve member 300 and the flushing inlet F (at the inlet opening 321), to a modified stopcock 100' where this fluid connection is automatically closed by a secondary valve function when the modified stopcock 100' is in one of its drug positions, and flushing is only possible in dedicated intermediate flushing positions where the fluid connection is open between the flushing inlet F and the main passageway 321.

Figure 13:
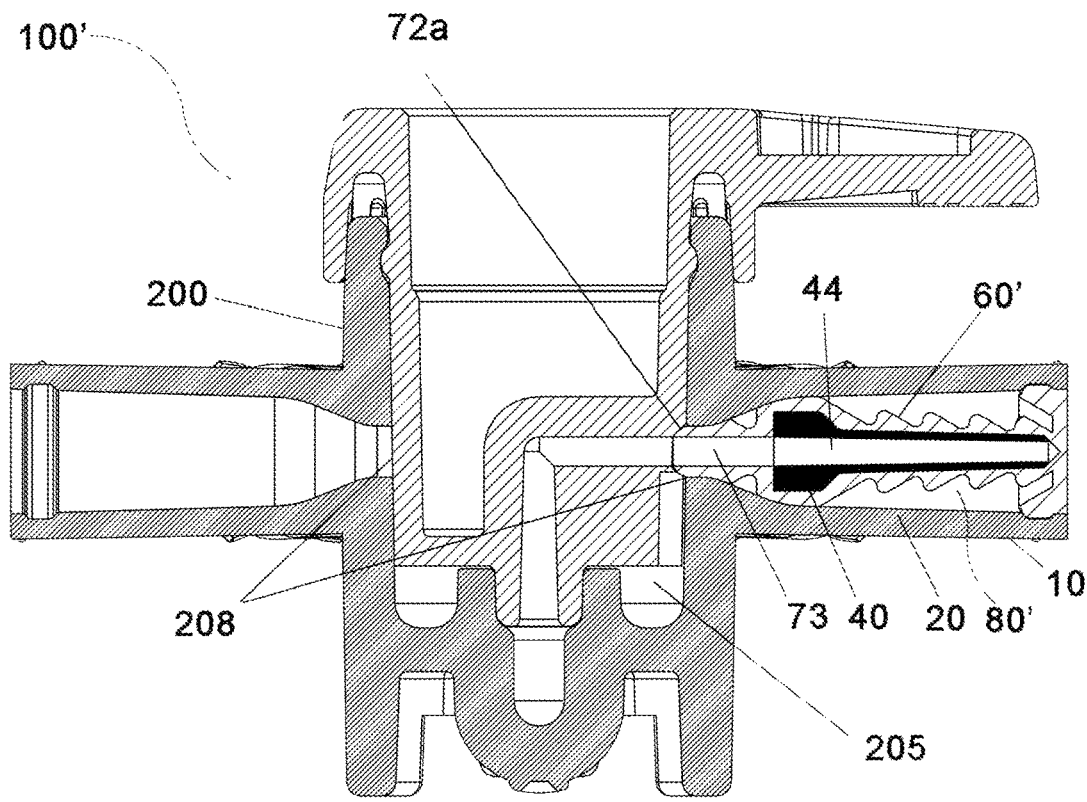
FIG. 13 is a cross-sectional view of a second embodiment of a medical stopcock comprising a second embodiment of a medical female connector according to the inventive concept.
Figure 14:
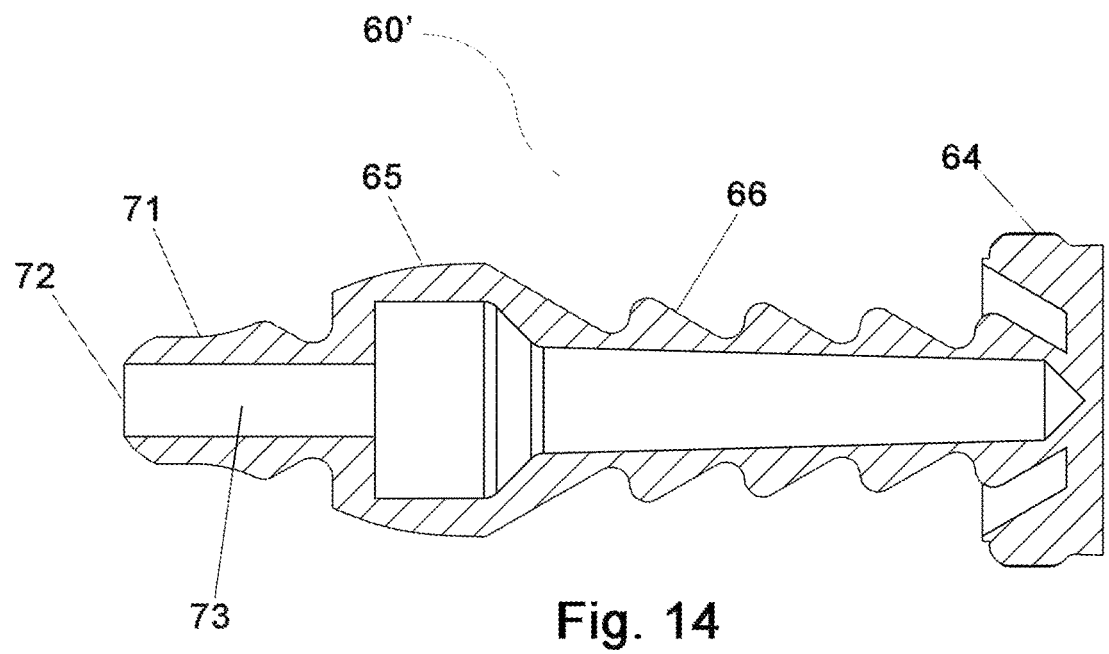
FIG. 14 is a cross-sectional view of a flexible valve member of the stopcock in FIG. 13.
Figure 15A:
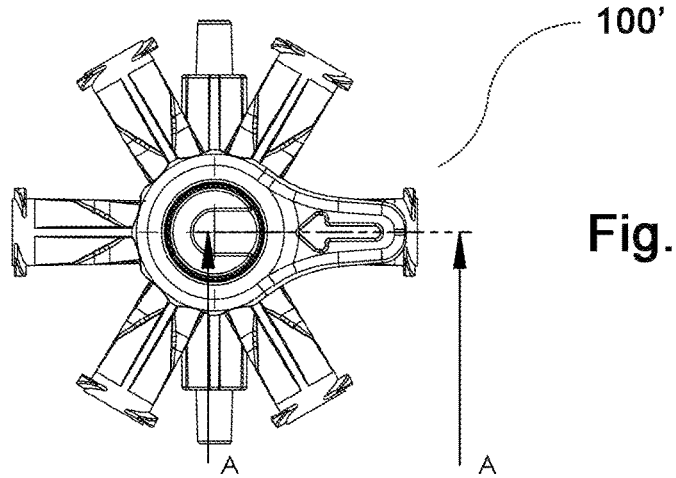
FIG. 15A to 15D show the stopcock in FIG. 13 in a first rotational position.
Figure 15B:
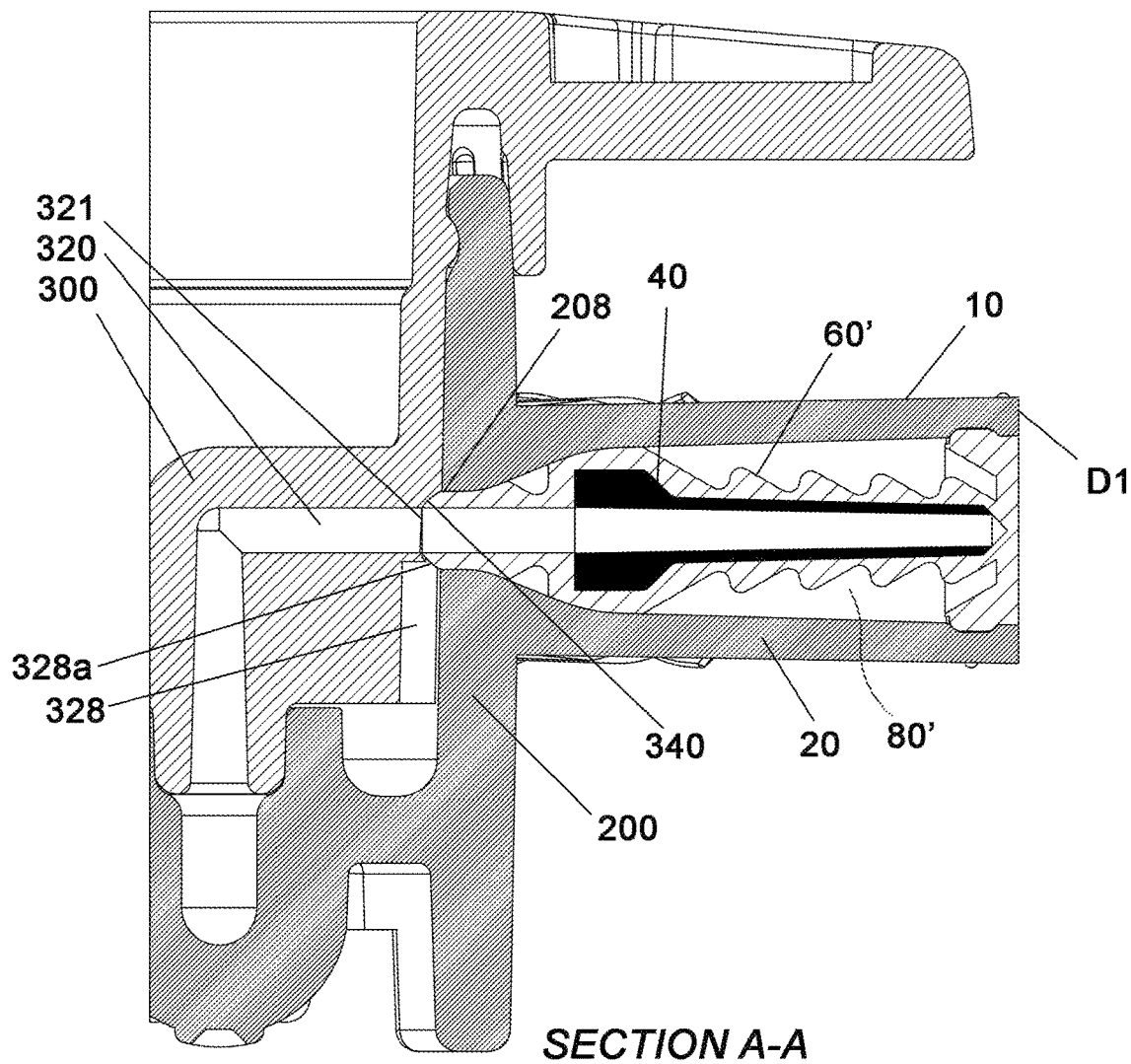
Figure 15C:
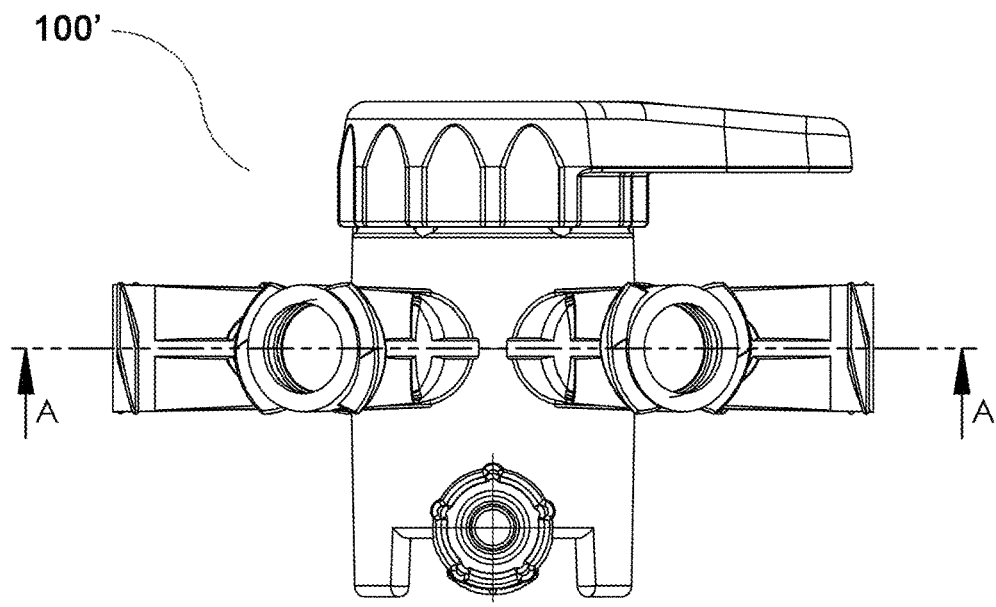

FIG. 13 illustrates an embodiment of a modified insert unit 80', which is inserted into the housing 20 of the female connector 10 of the modified stopcock 100'. FIG. 15B shows the relevant parts in larger scale. The plunger 40 of the modified insert unit 80' is unchanged, but the flexible valve member 60' is modified by presenting a distal extension part 71, which in this embodiment is integrally formed (molded) with the other parts 64, 65 and 66. The distal extension part 71 has an open distal end 72 and an inner fluid channel 73 in fluid communication with the inner channel 44 of the plunger 40. The distal extension part 71, which is also made of a flexible compressible material, is configured and dimensioned to be at least partly inserted through the associated opening 208 in the stopcock housing 200 to such an extent that a minor part 72*a* of the distal end 72 protrudes radially inside the inner cavity 205 of the stopcock housing 200 at the drug outlet opening 208. This projecting part 72*a* will operate as a flexible secondary valve member in combination with the rotary stopcock valve member 300 to form a secondary valve for controlling the fluid flow inside the stopcock housing 200 as will be described below. In the illustrated embodiment, there is a rotational symmetry formed in the radially outer part of the through-channel formed in the stopcock housing 200 at the drug outlet opening 208. The distal extension part 71 has a corresponding rotational symmetry such that it is brought to a predetermined axial sealed position when the insert unit 80' is inserted into the female connector housing 20, whereby the projecting part 72*a* may be correctly positioned in relation to the drug outlet opening 208.

Figure 15D:
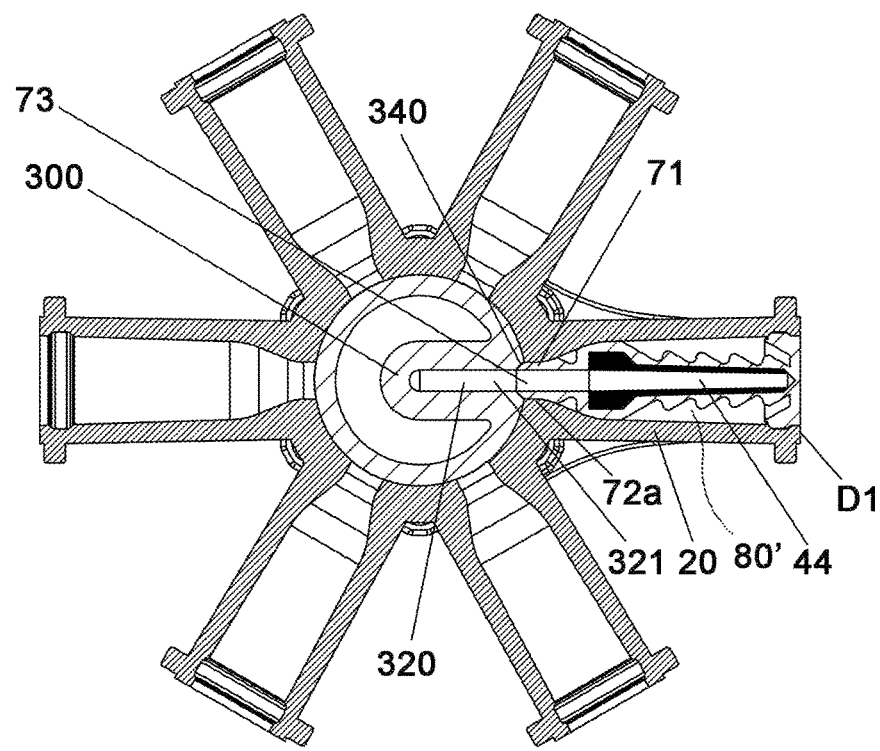

As best shown in the axial cross-section in FIG. 15B in combination with the radial cross-section in FIG. 15D, the cylindrical part of the rotary stopcock valve member 300 presents a radial recess or dimple 340. The inlet opening 321 of the main passageway 320 is located at the radial bottom of the dimple 340. As shown in the lateral cross-section in FIG. 15B, the axially upper end 328*a* of the axial transfer channel 328 also opens into the dimple 340. In the previous embodiment 100, there is always a fluid communication between inlet opening 321 and outlet opening 328*a* via the dimple 340, resulting in that flushing fluid is accessible in the drug positions also.

The modified stopcock 100' operates as follows. In each drug position, such as the D1 drug position shown in FIGS. 15A to 15D, the inlet opening 321 of the main passageway 320 in the rotary the stopcock valve member 300 is aligned with, and in fluid communication with, an associated drug outlet opening 208 in the stopcock housing 200, in the same way as in the previous embodiment 100. However, in this modified embodiment 100', the radially projecting part 72*a* of the flexible distal extension part 71 of the modified flexible valve member 60' projects into the dimple 340 in each drug position, forming an annular secondary valve member. In each drug position, the projecting part 72*a* acts as an annular valve member blocking the fluid connection in the dimple between the transfer channel 328 and the to the inlet opening 321 of the main passageway 320 in the rotary stopcock valve member 300, while the projecting part 71 still allows drug fluid to pass from the female connector 10 into the stopcock housing 200.

Figure 16A:
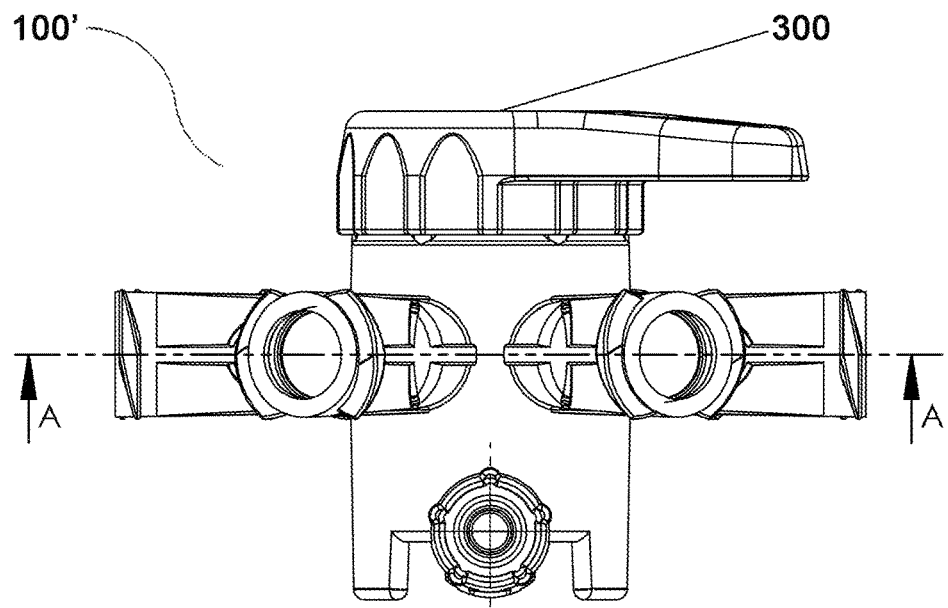
FIGS. 16A and 16B show the stopcock in FIG. 13 in a second rotational position.
Figure 16B:
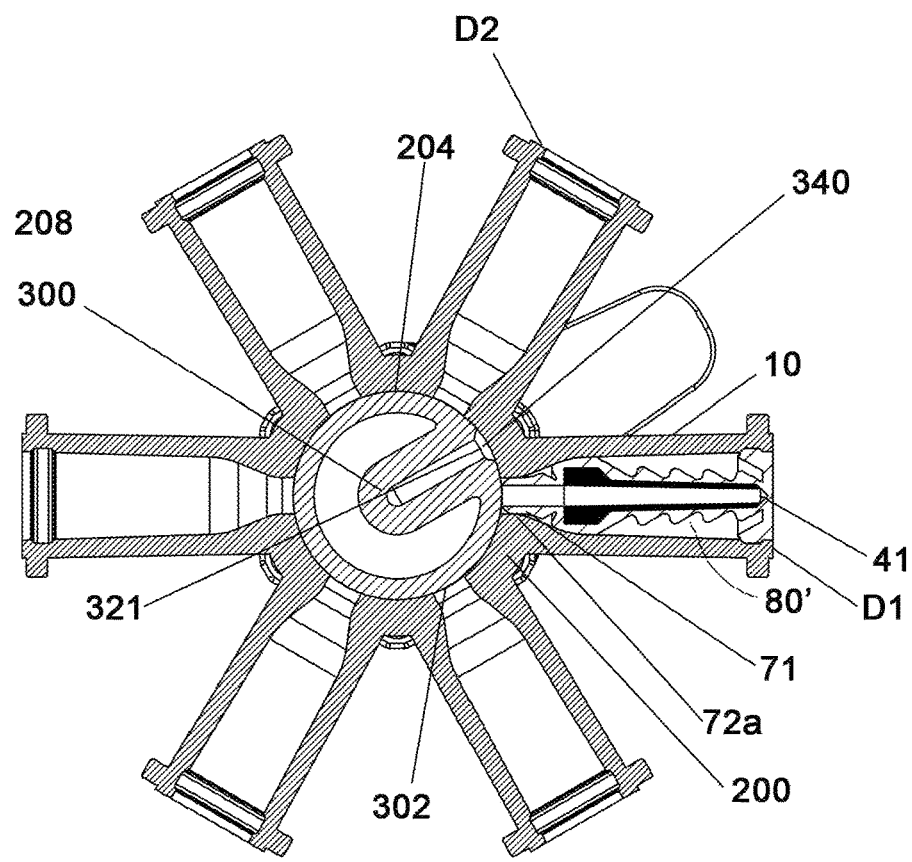

FIGS. 16A and 16B illustrate a flushing position of the modified stopcock 100', where the rotary stopcock valve member 300 has been rotated from its drug position to a flushing position between two drug positions (a flushing position between D1 and D2 is shown as an example). In this flushing position, the inlet opening 321 and the dimple 340 are circumferentially offset from the drug opening 208. The previously projecting part 72*a* of the flexible extension part 71 has now been pushed radially outwards by the rotary stopcock valve member 300 and into the wall of the stopcock housing 200. This part 72*a* is now inactive. The cylindrical outer surface 302 of the stopcock valve member 300 seals against the cylindrical inner surface 204 of the stopcock housing 200, preventing fluid flow between the female connector 10 and the valve housing 200.

In summary, by using a female connector according to the inventive concept, where the flexible valve member 60' in addition is provided with a flexible distal extension 71 extending partly into a stopcock housing 200 or the like, it becomes possible to achieve two different valve functions with one single insert 80': The first valve function at the proximal plunger end 41, and the secondary valve function at the distal end 72*a* of the extension part 71. It will be appreciated that it is an advantage that one and the same stopcock housing design may be manufactured and used for both types of valve functionality (100 or 100'), the only modification needed is the use of different insert types (80 or 80').

I claim:

1. A method for manufacturing a medical female connector for controlling a fluid flow, said method comprising:
   providing a housing having an inner cavity, which is defined by an inner surface of the housing and which extends from an open proximal end of the housing to an open distal end of the housing,
   wherein at least a part of the inner surface forms a frusto-conical female sealing surface, which defines a frusto-conical part of the inner cavity and which is arranged to be brought into sealing engagement with a conical part of a male connector insertable in said frusto-conical part of the inner cavity, said frusto-conical female sealing surface having a maximum diameter at the proximal end of the housing, and wherein the proximal end of the housing presents an entrance opening to the inner cavity with a diameter equal to or larger than the maximum diameter of the frusto-conical female sealing surface;

inserting a tubular plunger into the housing to a position in which the plunger extends inside the inner cavity, in a proximal direction towards the proximal end of the housing, from a distal end of the plunger to a proximal end of the plunger, wherein said plunger comprises an internal fluid channel extending from the proximal end of the plunger to the distal end of the plunger, and wherein the distal end of the plunger is located at a distance proximally from the distal end of the housing, and the proximal end of the plunger is located inside or proximally of said frusto-conical part of the inner cavity defined by the frusto-conical female sealing surface; and inserting a flexible valve member into the inner cavity to a position where the flexible valve member is movable between a flow stop configuration at which an initially closed proximal end of the flexible valve member is located proximally of the proximal end of the plunger and seals a flow path through the fluid channel of the plunger, and a flow configuration at which the proximal end of the flexible valve member is located distally of the proximal end of the plunger and is deformed by the plunger to allow a fluid flow through the fluid channel of the plunger, wherein, in the final manufactured female connector, the flexible valve member at its distal end presents a sealing part which forms a seal between the housing and the plunger and maintains the plunger positioned in relation to the housing; and further wherein the flexible valve member at its proximal end presents an engagement part of increased cross-section, and wherein the action of inserting the flexible valve member into the inner cavity comprises inserting the flexible valve member into the inner cavity to a position where said engagement part of the flexible valve member of increased cross-section is brought into mating engagement with an engagement groove formed in the inner surface of the housing when the flexible valve member is in the flow stop configuration, and further wherein the engagement part is not in mating engagement with the engagement groove when the flexible member is moved to be in the flow configuration.

2. The method according to claim 1, further comprising forming an insert unit including the plunger and the flexible valve member, wherein the action of inserting the plunger and the action of inserting the flexible valve member are performed in one step by inserting said insert unit into the inner cavity.

3. The method according to claim 2, wherein the action of forming said insert unit comprises molding the flexible valve member at least partly around the tubular plunger to form the insert unit.

4. The method according to claim 1, wherein the female sealing surface has a minimum diameter at a distal end thereof, and wherein the minimum diameter of the female sealing surface is larger or equal to any diameter of the inner cavity between the distal end of the female sealing surface and the distal end of the housing.

5. A medical female connector for controlling a fluid flow, comprising:
a housing having an inner cavity defined by an inner surface of the housing and extending from an open proximal end of the housing to an open distal end of the housing wherein:
at least a part of the inner surface forms a frusto-conical female sealing surface, which defines a frusto-conical part of the inner cavity and which is arranged to be brought into sealing engagement with a conical part of a male connector insertable in said frusto-conical part of the inner cavity, said frusto-conical female sealing surface having a maximum diameter at a proximal end of the female sealing surface and a minimum diameter at a distal end of the female sealing surface,
the proximal end of the housing presents an entrance opening to the inner cavity with a diameter equal to or larger than the maximum diameter of the female sealing surface, and
the minimum diameter of the female sealing surface is larger or equal to any diameter of the inner cavity between the distal end of the female sealing surface and the distal end of the housing;
a tubular plunger formed as a separate member from the housing and extending inside the inner cavity towards the entrance opening of the housing from a distal end of the plunger to a proximal end of the plunger, wherein said plunger comprises an internal fluid channel extending from the proximal end of the plunger to the distal end of the plunger, and wherein the distal end of the plunger is located at a distance proximally from the distal end of the housing; and
a flexible valve member being located in the inner cavity, having an initially closed proximal end, and being movable, in response to the male connector being connected to the female connector and engaging and distally moving said proximal end of the flexible valve member in relation to the proximal end of the plunger, between a flow stop configuration at which the proximal end of the flexible valve member is located proximally of the proximal end of the plunger and seals a flow path through the fluid channel of the plunger, and a flow configuration at which:
the proximal end of the flexible valve member is located distally of the proximal end of the plunger, and is deformed by the plunger to allow a fluid flow through the fluid channel of the plunger,
wherein the flexible valve member at a distal end thereof presents a sealing part which forms a seal between the housing and the plunger and maintains the plunger positioned in relation to the housing; and further
wherein the proximal end of the flexible valve member is provided with an engagement part of increased cross section, and the inner surface of the housing is provided with a mating engagement groove for receiving the engagement part of the flexible valve member, and wherein the engagement part and the engagement groove are situated such that that the engagement part mates with the engagement groove when the flexible valve member is in the flow stop configuration and such that the engagement part does not mate with the engagement groove when the flexible member is in the flow configuration.

6. The medical female connector according to claim 5, wherein the flexible valve member is compressible at least in a distal direction to assume its flow configuration in response to the male connector being connected to the female connector and engaging the proximal end of the flexible valve member.

7. The medical female connector according to claim 6, wherein the flexible valve member is a self-sealing type flexible valve member being structured and arranged to elastically expand and re-assume its flow stop configuration in response to the male connector being disconnected from the female connector.

8. The medical female connector according to claim 5, wherein the tubular plunger has a frusto-conical outer side, and the flexible valve member extends at least in part along the frusto-conical outer side of the plunger.

9. The medical female connector according to claim 5, wherein the plunger and the flexible valve member together form an insert unit configured and sized to be insertable as one single unit through the entrance opening and into the inner cavity of the female connector.

10. The medical female connector according to claim 9, wherein the flexible valve member is an elastomeric valve member molded at least partly around the plunger to form said insert unit.

11. The medical female connector according to claim 5, wherein the plunger is a single-piece element.

12. A medical female connector according to claim 5, comprising a stopcock housing, a stopcock valve member being rotatably received in the stopcock housing, and one or more closed-system type female connectors are arranged on an outside of the stopcock housing.

13. A medical connection assembly, comprising a medical female connector according to claim 5, and a male connector connected to the female connector, said male connector presenting a tubular insertion part being in an inserted position inside said frusto-conical part of the inner cavity of the female connector, wherein the tubular insertion part of the male connector presents an outer frusto-conical sealing surface being in sealing engagement with the frusto-conical sealing surface of the female connector, and wherein the proximal end of the plunger being received at least partly into the tubular insertion part of the male connector.

14. An assembly according to claim 13, wherein the tubular insertion part of the connected male connector is spaced from the tubular plunger of the female connector.

* * * * *